(12) United States Patent
Chin

(10) Patent No.: US 7,522,948 B2
(45) Date of Patent: Apr. 21, 2009

(54) MEDICAL SENSOR AND TECHNIQUE FOR USING THE SAME

(75) Inventor: Rodney P. Chin, Carson City, NV (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 399 days.

(21) Appl. No.: 11/415,711

(22) Filed: May 2, 2006

(65) Prior Publication Data
US 2007/0260130 A1 Nov. 8, 2007

(51) Int. Cl.
*A61B 5/1455* (2006.01)
(52) U.S. Cl. .................. 600/310; 600/323; 600/344
(58) Field of Classification Search .......... 600/310, 600/323, 344
See application file for complete search history.

(56) References Cited

U.S. PATENT DOCUMENTS

| | | | |
|---|---|---|---|
| 3,403,555 A | 10/1968 | Versaci et al. | |
| 3,536,545 A | 10/1970 | Traynor et al. | |
| D222,454 S | 10/1971 | Beeber | |
| 3,721,813 A | 3/1973 | Condon et al. | |
| 4,098,772 A | 7/1978 | Bonk et al. | |
| D250,275 S | 11/1978 | Bond | |
| D251,387 S | 3/1979 | Ramsey et al. | |
| D262,488 S | 12/1981 | Rossman et al. | |
| 4,334,544 A | 6/1982 | Hill et al. | |
| 4,350,165 A | 9/1982 | Striese | |
| 4,353,372 A | 10/1982 | Ayer | |
| 4,380,240 A | 4/1983 | Jobsis et al. | |
| 4,406,289 A | 9/1983 | Wesseling et al. | |
| 4,510,551 A | 4/1985 | Brainard, II | |
| 4,586,513 A | 5/1986 | Hamaguri | |
| 4,603,700 A | 8/1986 | Nichols et al. | |
| 4,621,643 A | 11/1986 | New, Jr. et al. | |
| 4,653,498 A | 3/1987 | New, Jr. et al. | |
| 4,677,528 A | 6/1987 | Miniet | |
| 4,694,833 A | 9/1987 | Hamaguri | |
| 4,697,593 A | 10/1987 | Evans et al. | |
| 4,700,708 A | 10/1987 | New, Jr. et al. | |
| 4,714,080 A | 12/1987 | Edgar, Jr. et al. | |

(Continued)

FOREIGN PATENT DOCUMENTS

DE     3405444     8/1985

(Continued)

OTHER PUBLICATIONS

Rheineck-Leyssius, Aart t., et al.; "Advanced Pulse Oximeter Signal Processing Technology Compared to Simple Averaging: I. Effect on Frequency of Alarms in the Operating Room," *Journal of clinical Anestesia*, vol. 11, pp. 192-195 (1990).

(Continued)

*Primary Examiner*—Eric F Winakur
*Assistant Examiner*—Etsub D Berhanu
(74) *Attorney, Agent, or Firm*—Fletcher Yoder

(57) ABSTRACT

A clip-style sensor may be constructed from materials having shape memory. A clip-style sensor is provided that is able to be flattened in order to simplify transport and storing. The sensors may be held flat by shipping restraints. Such a sensor is able to recover from being flattened and resume a curved shape.

51 Claims, 4 Drawing Sheets

U.S. PATENT DOCUMENTS

| | | | |
|---|---|---|---|
| 4,714,341 A | 12/1987 | Hamaguri et al. | |
| 4,722,120 A | 2/1988 | Lu | |
| 4,726,382 A | 2/1988 | Boehmer et al. | |
| 4,759,369 A | 7/1988 | Taylor | |
| 4,770,179 A | 9/1988 | New, Jr. et al. | |
| 4,773,422 A | 9/1988 | Isaacson et al. | |
| 4,776,339 A | 10/1988 | Schreiber | |
| 4,781,195 A | 11/1988 | Martin | |
| 4,783,815 A | 11/1988 | Buttner | |
| 4,796,636 A | 1/1989 | Branstetter et al. | |
| 4,800,495 A | 1/1989 | Smith | |
| 4,800,885 A | 1/1989 | Johnson | |
| 4,802,486 A | 2/1989 | Goodman et al. | |
| 4,805,623 A | 2/1989 | Jöbsis | |
| 4,807,630 A | 2/1989 | Malinouskas | |
| 4,807,631 A | 2/1989 | Hersh et al. | |
| 4,819,646 A | 4/1989 | Cheung et al. | |
| 4,819,752 A | 4/1989 | Zelin | |
| 4,824,242 A | 4/1989 | Frick et al. | |
| 4,825,872 A | 5/1989 | Tan et al. | |
| 4,825,879 A | 5/1989 | Tan et al. | |
| 4,830,014 A | 5/1989 | Goodman et al. | |
| 4,832,484 A | 5/1989 | Aoyagi et al. | |
| 4,846,183 A | 7/1989 | Martin | |
| 4,848,901 A | 7/1989 | Hood, Jr. | |
| 4,854,699 A | 8/1989 | Edgar, Jr. | |
| 4,859,056 A | 8/1989 | Prosser et al. | |
| 4,859,057 A | 8/1989 | Taylor et al. | |
| 4,863,265 A | 9/1989 | Flower et al. | |
| 4,865,038 A | 9/1989 | Rich et al. | |
| 4,867,557 A | 9/1989 | Takatani et al. | |
| 4,869,253 A | 9/1989 | Craig, Jr. et al. | |
| 4,869,254 A | 9/1989 | Stone et al. | |
| 4,880,304 A | 11/1989 | Jaeb et al. | |
| 4,883,055 A | 11/1989 | Merrick | |
| 4,883,353 A | 11/1989 | Hansmann et al. | |
| 4,890,619 A | 1/1990 | Hatschek | |
| 4,892,101 A | 1/1990 | Cheung et al. | |
| 4,901,238 A | 2/1990 | Suzuki et al. | |
| 4,908,762 A | 3/1990 | Suzuki et al. | |
| 4,911,167 A | 3/1990 | Corenman et al. | |
| 4,913,150 A | 4/1990 | Cheung et al. | |
| 4,926,867 A | 5/1990 | Kanda et al. | |
| 4,927,264 A | 5/1990 | Shiga et al. | |
| 4,928,692 A | 5/1990 | Goodman et al. | |
| 4,934,372 A | 6/1990 | Corenman et al. | |
| 4,938,218 A | 7/1990 | Goodman et al. | |
| 4,942,877 A | 7/1990 | Sakai et al. | |
| 4,948,248 A | 8/1990 | Lehman | |
| 4,955,379 A | 9/1990 | Hall | |
| 4,960,126 A | 10/1990 | Conlon et al. | |
| 4,964,408 A | 10/1990 | Hink et al. | |
| 4,971,062 A | 11/1990 | Hasebe et al. | |
| 4,974,591 A | 12/1990 | Awazu et al. | |
| 5,007,423 A | 4/1991 | Branstetter et al. | |
| 5,025,791 A | 6/1991 | Niwa | |
| RE33,643 E | 7/1991 | Isaacson et al. | |
| 5,028,787 A | 7/1991 | Rosenthal et al. | |
| 5,035,243 A | 7/1991 | Muz | |
| 5,040,539 A | 8/1991 | Schmitt et al. | |
| 5,041,187 A | 8/1991 | Hink et al. | |
| 5,054,488 A | 10/1991 | Muz | |
| 5,055,671 A | 10/1991 | Jones | |
| 5,058,588 A | 10/1991 | Kaestle | |
| 5,065,749 A | 11/1991 | Hasebe et al. | |
| 5,066,859 A | 11/1991 | Karkar et al. | |
| 5,069,213 A | 12/1991 | Polczynksi | |
| 5,078,136 A | 1/1992 | Stone et al. | |
| 5,086,229 A | 2/1992 | Rosenthal et al. | |
| 5,088,493 A | 2/1992 | Giannini et al. | |
| 5,090,410 A | 2/1992 | Saper et al. | |
| 5,094,239 A | 3/1992 | Jaeb et al. | |
| 5,094,240 A | 3/1992 | Muz | |
| 5,099,841 A | 3/1992 | Heinonen et al. | |
| 5,099,842 A | 3/1992 | Mannheimer et al. | |
| H001039 H | 4/1992 | Tripp et al. | |
| 5,104,623 A | 4/1992 | Miller | |
| 5,109,849 A | 5/1992 | Goodman et al. | |
| 5,111,817 A | 5/1992 | Clark et al. | |
| 5,113,861 A | 5/1992 | Rother | |
| D326,715 S | 6/1992 | Schmidt | |
| 5,125,403 A | 6/1992 | Culp | |
| 5,127,406 A | 7/1992 | Yamaguchi | |
| 5,131,391 A | 7/1992 | Sakai et al. | |
| 5,140,989 A | 8/1992 | Lewis et al. | |
| 5,152,296 A | 10/1992 | Simons | |
| 5,154,175 A | 10/1992 | Gunther | |
| 5,158,082 A | 10/1992 | Jones | |
| 5,170,786 A | 12/1992 | Thomas et al. | |
| 5,188,108 A | 2/1993 | Secker et al. | |
| 5,190,038 A | 3/1993 | Polson et al. | |
| 5,193,542 A | 3/1993 | Missanelli et al. | |
| 5,193,543 A | 3/1993 | Yelderman | |
| 5,203,329 A | 4/1993 | Takatani et al. | |
| 5,209,230 A | 5/1993 | Swedlow et al. | |
| 5,213,099 A | 5/1993 | Tripp et al. | |
| 5,216,598 A | 6/1993 | Branstetter et al. | |
| 5,217,012 A | 6/1993 | Young et al. | |
| 5,217,013 A | 6/1993 | Lewis et al. | |
| 5,218,207 A | 6/1993 | Rosenthal | |
| 5,218,962 A | 6/1993 | Mannheimer et al. | |
| 5,224,478 A | 7/1993 | Sakai et al. | |
| 5,226,417 A | 7/1993 | Swedlow et al. | |
| 5,228,440 A | 7/1993 | Chung et al. | |
| 5,237,994 A | 8/1993 | Goldberger | |
| 5,239,185 A | 8/1993 | Ito et al. | |
| 5,246,002 A | 9/1993 | Prosser | |
| 5,246,003 A | 9/1993 | DeLonzor | |
| 5,247,931 A | 9/1993 | Norwood | |
| 5,247,932 A | 9/1993 | Chung et al. | |
| 5,249,576 A | 10/1993 | Goldberger et al. | |
| 5,253,645 A | 10/1993 | Friedman et al. | |
| 5,253,646 A | 10/1993 | Delpy et al. | |
| 5,259,381 A | 11/1993 | Cheung et al. | |
| 5,259,761 A | 11/1993 | Schnettler et al. | |
| 5,263,244 A | 11/1993 | Centa et al. | |
| 5,267,562 A | 12/1993 | Ukawa et al. | |
| 5,267,563 A | 12/1993 | Swedlow et al. | |
| 5,267,566 A | 12/1993 | Choucair et al. | |
| 5,273,036 A | 12/1993 | Kronberg et al. | |
| 5,275,159 A | 1/1994 | Griebel | |
| 5,278,627 A | 1/1994 | Aoyagi et al. | |
| 5,279,295 A | 1/1994 | Martens et al. | |
| 5,285,783 A | 2/1994 | Secker | |
| 5,285,784 A | 2/1994 | Seeker | |
| 5,287,853 A | 2/1994 | Vester et al. | |
| 5,291,884 A | 3/1994 | Heinemann et al. | |
| 5,297,548 A | 3/1994 | Pologe | |
| 5,299,120 A | 3/1994 | Kaestle | |
| 5,299,570 A | 4/1994 | Hatschek | |
| 5,309,908 A | 5/1994 | Freidman et al. | |
| 5,311,865 A | 5/1994 | Mayeux | |
| 5,313,940 A | 5/1994 | Fuse et al. | |
| 5,323,776 A | 6/1994 | Blakely et al. | |
| 5,329,922 A | 7/1994 | Atlee, III | |
| 5,337,744 A | 8/1994 | Branigan | |
| 5,339,810 A | 8/1994 | Ivers et al. | |
| 5,343,818 A | 9/1994 | McCarthy et al. | |
| 5,343,869 A | 9/1994 | Pross et al. | |
| 5,348,003 A | 9/1994 | Caro | |
| 5,348,004 A | 9/1994 | Hollub et al. | |
| 5,348,005 A | 9/1994 | Merrick et al. | |
| 5,349,519 A | 9/1994 | Kaestle | |
| 5,349,952 A | 9/1994 | McCarthy et al. | |

| | | | | | |
|---|---|---|---|---|---|
| 5,349,953 A | 9/1994 | McCarthy et al. | 5,582,169 A | 12/1996 | Oda et al. |
| 5,351,685 A | 10/1994 | Potratz | 5,584,296 A | 12/1996 | Cui et al. |
| 5,353,799 A | 10/1994 | Chance | 5,588,425 A | 12/1996 | Sackner et al. |
| 5,355,880 A | 10/1994 | Thomas et al. | 5,588,427 A | 12/1996 | Tien |
| 5,355,882 A | 10/1994 | Ukawa et al. | 5,590,652 A | 1/1997 | Inai |
| 5,361,758 A | 11/1994 | Hall et al. | 5,595,176 A | 1/1997 | Yamaura |
| 5,365,066 A | 11/1994 | Krueger, Jr. et al. | 5,596,986 A | 1/1997 | Goldfarb |
| 5,368,025 A | 11/1994 | Young et al. | 5,611,337 A | 3/1997 | Bukta |
| 5,368,026 A | 11/1994 | Swedlow et al. | 5,617,852 A | 4/1997 | MacGregor |
| 5,368,224 A | 11/1994 | Richardson et al. | 5,619,991 A | 4/1997 | Sloane |
| 5,372,136 A | 12/1994 | Steuer et al. | 5,619,992 A | 4/1997 | Guthrie et al. |
| 5,377,675 A | 1/1995 | Ruskewicz et al. | 5,626,140 A | 5/1997 | Feldman et al. |
| 5,385,143 A | 1/1995 | Aoyagi | 5,630,413 A | 5/1997 | Thomas et al. |
| 5,387,122 A | 2/1995 | Goldberger et al. | 5,632,272 A | 5/1997 | Diab et al. |
| 5,390,670 A | 2/1995 | Centa et al. | 5,632,273 A | 5/1997 | Suzuki |
| 5,392,777 A | 2/1995 | Swedlow et al. | 5,634,459 A | 6/1997 | Gardosi |
| 5,398,680 A | 3/1995 | Polson et al. | 5,638,593 A | 6/1997 | Gerhardt et al. |
| 5,402,777 A | 4/1995 | Warring et al. | 5,638,816 A | 6/1997 | Kiani-Azarbayjany et al. |
| 5,402,779 A | 4/1995 | Chen et al. | 5,638,818 A | 6/1997 | Diab et al. |
| 5,411,023 A | 5/1995 | Morris, Sr. et al. | 5,645,060 A | 7/1997 | Yorkey et al. |
| 5,411,024 A | 5/1995 | Thomas et al. | 5,645,440 A | 7/1997 | Tobler et al. |
| 5,413,099 A | 5/1995 | Schmidt et al. | 5,660,567 A | 8/1997 | Nierlich et al. |
| 5,413,100 A | 5/1995 | Barthelemy et al. | 5,662,105 A | 9/1997 | Tien |
| 5,413,101 A | 5/1995 | Sugiura | 5,662,106 A | 9/1997 | Swedlow et al. |
| 5,413,102 A | 5/1995 | Schmidt et al. | 5,664,270 A | 9/1997 | Bell et al. |
| 5,417,207 A | 5/1995 | Young et al. | 5,666,952 A | 9/1997 | Fuse et al. |
| 5,421,329 A | 6/1995 | Casciani et al. | 5,671,529 A | 9/1997 | Nelson |
| 5,425,360 A | 6/1995 | Nelson | 5,673,692 A | 10/1997 | Schulze et al. |
| 5,425,362 A | 6/1995 | Siker et al. | 5,673,693 A | 10/1997 | Solenberger |
| 5,427,093 A | 6/1995 | Ogawa et al. | 5,676,139 A | 10/1997 | Goldberger et al. |
| 5,429,128 A | 7/1995 | Cadell et al. | 5,676,141 A | 10/1997 | Hollub |
| 5,429,129 A | 7/1995 | Lovejoy et al. | 5,678,544 A | 10/1997 | DeLonzor et al. |
| 5,431,159 A | 7/1995 | Baker et al. | 5,680,857 A | 10/1997 | Pelikan et al. |
| 5,431,170 A | 7/1995 | Mathews | 5,685,299 A | 11/1997 | Diab et al. |
| 5,437,275 A | 8/1995 | Amundsen et al. | 5,685,301 A | 11/1997 | Klomhaus |
| 5,438,986 A | 8/1995 | Disch et al. | 5,687,719 A | 11/1997 | Sato et al. |
| 5,448,991 A | 9/1995 | Polson et al. | 5,687,722 A | 11/1997 | Tien et al. |
| 5,452,717 A | 9/1995 | Branigan et al. | 5,692,503 A | 12/1997 | Kuenstner |
| 5,465,714 A | 11/1995 | Scheuing | 5,692,505 A | 12/1997 | Fouts |
| 5,469,845 A | 11/1995 | DeLonzor et al. | 5,709,205 A | 1/1998 | Bukta |
| RE35,122 E | 12/1995 | Corenman et al. | 5,713,355 A | 2/1998 | Richardson et al. |
| 5,482,034 A | 1/1996 | Lewis et al. | 5,724,967 A | 3/1998 | Venkatachalam |
| 5,482,036 A | 1/1996 | Diab et al. | 5,727,547 A | 3/1998 | Levinson et al. |
| 5,485,847 A | 1/1996 | Baker, Jr. | 5,730,124 A | 3/1998 | Yamauchi |
| 5,490,505 A | 2/1996 | Diab et al. | 5,731,582 A | 3/1998 | West |
| 5,490,523 A | 2/1996 | Isaacson et al. | D393,830 S | 4/1998 | Tobler et al. |
| 5,491,299 A | 2/1996 | Naylor et al. | 5,743,260 A | 4/1998 | Chung et al. |
| 5,494,032 A | 2/1996 | Robinson et al. | 5,743,262 A | 4/1998 | Lepper, Jr. et al. |
| 5,494,043 A | 2/1996 | O'Sullivan et al. | 5,743,263 A | 4/1998 | Baker, Jr. |
| 5,497,771 A | 3/1996 | Rosenheimer | 5,746,206 A | 5/1998 | Mannheimer |
| 5,499,627 A | 3/1996 | Steuer et al. | 5,746,697 A | 5/1998 | Swedlow et al. |
| 5,503,148 A | 4/1996 | Pologe et al. | 5,752,914 A | 5/1998 | DeLonzor et al. |
| 5,505,199 A | 4/1996 | Kim | 5,755,226 A | 5/1998 | Carim et al. |
| 5,507,286 A | 4/1996 | Solenberger | 5,758,644 A | 6/1998 | Diab et al. |
| 5,511,546 A | 4/1996 | Hon | 5,760,910 A | 6/1998 | Lepper, Jr. et al. |
| 5,517,988 A | 5/1996 | Gerhard | 5,766,125 A | 6/1998 | Aoyagi et al. |
| 5,520,177 A | 5/1996 | Ogawa et al. | 5,766,127 A | 6/1998 | Pologe et al. |
| 5,521,851 A | 5/1996 | Wei et al. | 5,769,785 A | 6/1998 | Diab et al. |
| 5,522,388 A | 6/1996 | Ishikawa et al. | 5,772,587 A | 6/1998 | Gratton et al. |
| 5,524,617 A | 6/1996 | Mannheimer | 5,774,213 A | 6/1998 | Trebino et al. |
| 5,529,064 A | 6/1996 | Rall et al. | 5,776,058 A | 7/1998 | Levinson et al. |
| 5,533,507 A | 7/1996 | Potratz et al. | 5,776,059 A | 7/1998 | Kaestle |
| 5,551,423 A | 9/1996 | Sugiura | 5,779,630 A | 7/1998 | Fein et al. |
| 5,551,424 A | 9/1996 | Morrison et al. | 5,782,237 A | 7/1998 | Casciani et al. |
| 5,553,614 A | 9/1996 | Chance | 5,782,756 A | 7/1998 | Mannheimer |
| 5,553,615 A | 9/1996 | Carim et al. | 5,782,757 A | 7/1998 | Diab et al. |
| 5,555,882 A | 9/1996 | Richardson et al. | 5,782,758 A | 7/1998 | Ausec et al. |
| 5,558,096 A | 9/1996 | Palatnik | 5,786,592 A | 7/1998 | Hök |
| 5,560,355 A | 10/1996 | Merchant et al. | 5,788,634 A | 8/1998 | Suda et al. |
| 5,564,417 A | 10/1996 | Chance | 5,790,729 A | 8/1998 | Pologe et al. |
| 5,575,284 A | 11/1996 | Athan et al. | 5,792,052 A | 8/1998 | Isaacson et al. |
| 5,575,285 A | 11/1996 | Takanashi et al. | 5,795,292 A | 8/1998 | Lewis et al. |
| 5,577,500 A | 11/1996 | Potratz | 5,797,841 A | 8/1998 | DeLonzor et al. |

| Patent No. | Date | Inventor(s) | Patent No. | Date | Inventor(s) |
|---|---|---|---|---|---|
| 5,800,348 A | 9/1998 | Kaestle | 5,995,855 A | 11/1999 | Kiani et al. |
| 5,800,349 A | 9/1998 | Isaacson et al. | 5,995,856 A | 11/1999 | Mannheimer et al. |
| 5,803,910 A | 9/1998 | Potratz | 5,995,858 A | 11/1999 | Kinast |
| 5,807,246 A | 9/1998 | Sakaguchi et al. | 5,995,859 A | 11/1999 | Takahashi |
| 5,807,247 A | 9/1998 | Merchant et al. | 5,997,343 A | 12/1999 | Mills et al. |
| 5,807,248 A | 9/1998 | Mills | 5,999,834 A | 12/1999 | Wang et al. |
| 5,810,723 A | 9/1998 | Aldrich | 6,002,952 A | 12/1999 | Diab et al. |
| 5,810,724 A | 9/1998 | Gronvall | 6,005,658 A | 12/1999 | Kaluza et al. |
| 5,813,980 A | 9/1998 | Levinson et al. | 6,006,120 A | 12/1999 | Levin |
| 5,817,008 A | 10/1998 | Rafert et al. | 6,011,985 A | 1/2000 | Athan et al. |
| 5,817,009 A | 10/1998 | Rosenheimer et al. | 6,011,986 A | 1/2000 | Diab et al. |
| 5,817,010 A | 10/1998 | Hibl | 6,014,576 A | 1/2000 | Raley et al. |
| 5,818,985 A | 10/1998 | Merchant et al. | 6,018,673 A | 1/2000 | Chin et al. |
| 5,820,550 A | 10/1998 | Polson et al. | 6,018,674 A | 1/2000 | Aronow |
| 5,823,950 A | 10/1998 | Diab et al. | 6,022,321 A | 2/2000 | Amano et al. |
| 5,823,952 A | 10/1998 | Levinson et al. | 6,023,541 A | 2/2000 | Merchant et al. |
| 5,827,179 A | 10/1998 | Lichter et al. | 6,026,312 A | 2/2000 | Shemwell et al. |
| 5,827,182 A | 10/1998 | Raley et al. | 6,026,314 A | 2/2000 | Amerov et al. |
| 5,829,439 A | 11/1998 | Yokosawa et al. | 6,031,603 A | 2/2000 | Fine et al. |
| 5,830,135 A | 11/1998 | Bosque et al. | 6,035,223 A | 3/2000 | Baker, Jr. |
| 5,830,136 A | 11/1998 | DeLonzor et al. | 6,036,642 A | 3/2000 | Diab et al. |
| 5,830,137 A | 11/1998 | Scharf | 6,041,247 A | 3/2000 | Weckstrom et al. |
| 5,839,439 A | 11/1998 | Nierlich et al. | 6,044,283 A | 3/2000 | Fein et al. |
| RE36,000 E | 12/1998 | Swedlow et al. | 6,047,201 A | 4/2000 | Jackson, III |
| 5,842,979 A | 12/1998 | Jarman et al. | 6,055,447 A | 4/2000 | Well |
| 5,842,981 A | 12/1998 | Larsen et al. | 6,061,584 A | 5/2000 | Lovejoy et al. |
| 5,842,982 A | 12/1998 | Mannheimer | 6,064,898 A | 5/2000 | Aldrich |
| 5,846,190 A | 12/1998 | Woehrle | 6,064,899 A | 5/2000 | Fein et al. |
| 5,851,178 A | 12/1998 | Aronow | 6,067,462 A | 5/2000 | Diab et al. |
| 5,851,179 A | 12/1998 | Ritson et al. | 6,073,038 A | 6/2000 | Wang et al. |
| 5,853,364 A | 12/1998 | Baker, Jr. et al. | 6,078,829 A | 6/2000 | Uchida |
| 5,860,919 A | 1/1999 | Kiani-Azarbayjany et al. | 6,078,833 A | 6/2000 | Hueber |
| 5,865,736 A | 2/1999 | Baker, Jr. et al. | 6,081,735 A | 6/2000 | Diab et al. |
| 5,879,294 A | 3/1999 | Anderson et al. | 6,083,157 A | 7/2000 | Noller |
| 5,885,213 A | 3/1999 | Richardson et al. | 6,083,172 A | 7/2000 | Baker, Jr. et al. |
| 5,890,929 A | 4/1999 | Mills et al. | 6,088,607 A | 7/2000 | Diab et al. |
| 5,891,021 A | 4/1999 | Dillon et al. | 6,094,592 A | 7/2000 | Yorkey et al. |
| 5,891,022 A | 4/1999 | Pologe | 6,095,974 A | 8/2000 | Shemwell et al. |
| 5,891,024 A | 4/1999 | Jarman et al. | 6,104,938 A | 8/2000 | Huiku et al. |
| 5,891,025 A | 4/1999 | Buschmann et al. | 6,104,939 A | 8/2000 | Groner |
| 5,891,026 A | 4/1999 | Wang et al. | 6,112,107 A | 8/2000 | Hannula |
| 5,902,235 A | 5/1999 | Lewis et al. | 6,113,541 A | 9/2000 | Dias et al. |
| 5,910,108 A | 6/1999 | Solenberger | 6,115,621 A | 9/2000 | Chin |
| 5,911,690 A | 6/1999 | Rall | 6,122,535 A | 9/2000 | Kaestle et al. |
| 5,912,656 A | 6/1999 | Tham et al. | 6,133,994 A | 10/2000 | Mathews et al. |
| 5,913,819 A | 6/1999 | Taylor et al. | 6,135,952 A | 10/2000 | Coetzee |
| 5,916,154 A | 6/1999 | Hobbs et al. | 6,144,444 A | 11/2000 | Haworth et al. |
| 5,916,155 A | 6/1999 | Levinson et al. | 6,144,867 A | 11/2000 | Walker et al. |
| 5,919,133 A | 7/1999 | Taylor et al. | 6,144,868 A | 11/2000 | Parker |
| 5,919,134 A | 7/1999 | Diab | 6,149,481 A | 11/2000 | Wang et al. |
| 5,920,263 A | 7/1999 | Huttenhoff et al. | 6,151,107 A | 11/2000 | Schöllerman et al. |
| 5,921,921 A | 7/1999 | Potratz et al. | 6,151,516 A | 11/2000 | Kiani-Azarbayjani et al. |
| 5,922,607 A | 7/1999 | Bernreuter | 6,151,518 A | 11/2000 | Hayashi |
| 5,924,979 A | 7/1999 | Swedlow et al. | 6,152,754 A | 11/2000 | Gerhardt et al. |
| 5,924,980 A | 7/1999 | Coetzee | 6,154,667 A | 11/2000 | Miura et al. |
| 5,924,982 A | 7/1999 | Chin | 6,157,850 A | 12/2000 | Diab et al. |
| 5,924,985 A | 7/1999 | Jones | 6,159,147 A | 12/2000 | Lichter |
| 5,934,277 A | 8/1999 | Mortz | 6,163,715 A | 12/2000 | Larsen et al. |
| 5,934,925 A | 8/1999 | Tobler et al. | 6,165,005 A | 12/2000 | Mills et al. |
| 5,940,182 A | 8/1999 | Lepper, Jr. et al. | 6,173,196 B1 | 1/2001 | Delonzor et al. |
| 5,954,644 A | 9/1999 | Dettling et al. | 6,178,343 B1 | 1/2001 | Bindszus et al. |
| 5,957,840 A | 9/1999 | Terasawa et al. | 6,179,159 B1 | 1/2001 | Gurley |
| 5,960,610 A | 10/1999 | Levinson et al. | 6,181,958 B1 | 1/2001 | Steuer et al. |
| 5,961,450 A | 10/1999 | Merchant et al. | 6,181,959 B1 | 1/2001 | Schöllerman et al. |
| 5,961,452 A | 10/1999 | Chung et al. | 6,184,521 B1 | 2/2001 | Coffin, IV et al. |
| 5,964,701 A | 10/1999 | Asada et al. | 6,188,470 B1 | 2/2001 | Grace |
| 5,971,930 A | 10/1999 | Elghazzawi | 6,192,260 B1 | 2/2001 | Chance |
| 5,978,691 A | 11/1999 | Mills | 6,195,575 B1 | 2/2001 | Levinson |
| 5,978,693 A | 11/1999 | Hamilton et al. | 6,198,951 B1 | 3/2001 | Kosuda et al. |
| 5,983,120 A | 11/1999 | Groner et al. | 6,206,830 B1 | 3/2001 | Diab et al. |
| 5,983,122 A | 11/1999 | Jarman et al. | 6,213,952 B1 | 4/2001 | Finarov et al. |
| 5,987,343 A | 11/1999 | Kinast | 6,217,523 B1 | 4/2001 | Amano et al. |
| 5,991,648 A | 11/1999 | Levin | 6,222,189 B1 | 4/2001 | Misner et al. |

| | | |
|---|---|---|
| 6,223,064 B1 | 4/2001 | Lynn |
| 6,226,539 B1 | 5/2001 | Potratz |
| 6,226,540 B1 | 5/2001 | Bernreuter et al. |
| 6,229,856 B1 | 5/2001 | Diab et al. |
| 6,230,035 B1 | 5/2001 | Aoyagi et al. |
| 6,233,470 B1 | 5/2001 | Tsuchiya |
| 6,236,871 B1 | 5/2001 | Tsuchiya |
| 6,236,872 B1 | 5/2001 | Diab et al. |
| 6,240,305 B1 | 5/2001 | Tsuchiya |
| 6,253,097 B1 | 6/2001 | Aronow et al. |
| 6,253,098 B1 | 6/2001 | Walker et al. |
| 6,256,523 B1 | 7/2001 | Diab et al. |
| 6,256,524 B1 | 7/2001 | Walker et al. |
| 6,261,236 B1 | 7/2001 | Grinblatov |
| 6,263,221 B1 | 7/2001 | Chance et al. |
| 6,263,222 B1 | 7/2001 | Diab et al. |
| 6,263,223 B1 | 7/2001 | Sheperd et al. |
| 6,266,546 B1 | 7/2001 | Steuer et al. |
| 6,266,547 B1 | 7/2001 | Walker et al. |
| 6,272,363 B1 | 8/2001 | Casciani et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,894 B1 | 9/2001 | Oppelt et al. |
| 6,285,895 B1 | 9/2001 | Ristolainen et al. |
| 6,285,896 B1 | 9/2001 | Tobler et al. |
| 6,298,252 B1 | 10/2001 | Kovach et al. |
| 6,308,089 B1 | 10/2001 | Von der Ruhr et al. |
| 6,321,100 B1 | 11/2001 | Parker |
| 6,330,468 B1 | 12/2001 | Scharf |
| 6,334,065 B1 | 12/2001 | Al-Ali et al. |
| 6,339,715 B1 | 1/2002 | Bahr et al. |
| 6,342,039 B1 | 1/2002 | Lynn |
| 6,343,223 B1 | 1/2002 | Chin et al. |
| 6,343,224 B1 | 1/2002 | Parker |
| 6,349,228 B1 | 2/2002 | Kiani et al. |
| 6,351,658 B1 | 2/2002 | Middleman et al. |
| 6,353,750 B1 | 3/2002 | Kimura |
| 6,356,774 B1 | 3/2002 | Bernstein et al. |
| 6,360,113 B1 | 3/2002 | Dettling |
| 6,360,114 B1 | 3/2002 | Diab et al. |
| 6,361,501 B1 | 3/2002 | Amano et al. |
| 6,363,269 B1 | 3/2002 | Hanna et al. |
| D455,834 S | 4/2002 | Donars et al. |
| 6,370,408 B1 | 4/2002 | Merchant et al. |
| 6,370,409 B1 | 4/2002 | Chung et al. |
| 6,371,921 B1 | 4/2002 | Caro |
| 6,374,129 B1 | 4/2002 | Chin et al. |
| 6,377,829 B1 | 4/2002 | Al-Ali et al. |
| 6,381,479 B1 | 4/2002 | Norris |
| 6,381,480 B1 | 4/2002 | Stoddar et al. |
| 6,385,471 B1 | 5/2002 | Mortz |
| 6,385,821 B1 | 5/2002 | Modgil et al. |
| 6,388,240 B2 | 5/2002 | Schulz et al. |
| 6,393,310 B1 | 5/2002 | Kuenster |
| 6,393,311 B1 | 5/2002 | Edgar, Jr. et al. |
| 6,397,091 B2 | 5/2002 | Diab et al. |
| 6,397,092 B1 | 5/2002 | Norris et al. |
| 6,397,093 B1 | 5/2002 | Aldrich |
| D458,226 S | 6/2002 | Chin et al. |
| 6,400,971 B1 | 6/2002 | Finarov et al. |
| 6,400,972 B1 | 6/2002 | Fine |
| 6,400,973 B1 | 6/2002 | Winter |
| 6,402,690 B1 | 6/2002 | Rhee et al. |
| 6,408,198 B1 | 6/2002 | Hanna et al. |
| 6,411,832 B1 | 6/2002 | Guthermann |
| 6,411,833 B1 | 6/2002 | Baker, Jr. et al. |
| 6,421,549 B1 | 7/2002 | Jacques |
| 6,430,423 B2 | 8/2002 | DeLonzor et al. |
| 6,430,513 B1 | 8/2002 | Wang et al. |
| 6,430,525 B1 | 8/2002 | Weber et al. |
| 6,434,408 B1 | 8/2002 | Heckel et al. |
| 6,438,396 B1 | 8/2002 | Cook |
| 6,438,399 B1 | 8/2002 | Kurth |
| 6,449,501 B1 | 9/2002 | Reuss |
| 6,453,183 B1 | 9/2002 | Walker |
| 6,453,184 B1 | 9/2002 | Hyogo et al. |
| 6,456,862 B2 | 9/2002 | Benni |
| 6,461,305 B1 | 10/2002 | Schnall |
| 6,463,310 B1 | 10/2002 | Swedlow et al. |
| 6,463,311 B1 | 10/2002 | Diab |
| 6,466,808 B1 | 10/2002 | Chin et al. |
| 6,466,809 B1 | 10/2002 | Riley |
| 6,470,199 B1 | 10/2002 | Kopotic et al. |
| 6,470,200 B2 | 10/2002 | Walker et al. |
| 6,480,729 B2 | 11/2002 | Stone |
| 6,490,466 B1 | 12/2002 | Fein et al. |
| 6,493,568 B1 | 12/2002 | Bell |
| 6,496,711 B1 | 12/2002 | Athan et al. |
| 6,498,942 B1 | 12/2002 | Esenaliev et al. |
| 6,501,974 B2 | 12/2002 | Huiku |
| 6,501,975 B2 | 12/2002 | Diab et al. |
| 6,505,060 B1 | 1/2003 | Norris |
| 6,505,061 B2 | 1/2003 | Larson |
| 6,505,133 B1 | 1/2003 | Hanna et al. |
| 6,510,329 B2 | 1/2003 | Heckel |
| 6,510,331 B1 | 1/2003 | Williams et al. |
| 6,512,937 B2 | 1/2003 | Blank et al. |
| 6,515,273 B2 | 2/2003 | Al-Ali |
| 6,519,484 B1 | 2/2003 | Lovejoy et al. |
| 6,519,486 B1 | 2/2003 | Edgar, Jr. et al. |
| 6,519,487 B1 | 2/2003 | Parker |
| 6,525,386 B1 | 2/2003 | Mills et al. |
| 6,526,300 B1 | 2/2003 | Kiani et al. |
| 6,526,301 B2 | 2/2003 | Larsen et al. |
| 6,541,756 B2 | 4/2003 | Schulz et al. |
| 6,542,764 B1 | 4/2003 | Al-Ali et al. |
| 6,546,267 B1 | 4/2003 | Sugiura et al. |
| 6,553,241 B2 | 4/2003 | Mannheimer et al. |
| 6,553,242 B1 | 4/2003 | Sarussi |
| 6,553,243 B2 | 4/2003 | Gurley |
| 6,554,788 B1 | 4/2003 | Hunley |
| 6,556,852 B1 | 4/2003 | Schulze et al. |
| 6,560,470 B1 | 5/2003 | Pologe |
| 6,564,077 B2 | 5/2003 | Mortara |
| 6,564,088 B1 | 5/2003 | Soller et al. |
| 6,571,113 B1 | 5/2003 | Fein et al. |
| 6,571,114 B1 | 5/2003 | Koike et al. |
| 6,574,491 B2 | 6/2003 | Elghazzawi |
| 6,580,086 B1 | 6/2003 | Schulz et al. |
| 6,584,336 B1 | 6/2003 | Ali et al. |
| 6,587,703 B2 | 7/2003 | Cheng et al. |
| 6,587,704 B1 | 7/2003 | Fine et al. |
| 6,589,172 B2 | 7/2003 | Williams et al. |
| 6,591,122 B2 | 7/2003 | Schmitt |
| 6,591,123 B2 | 7/2003 | Fein et al. |
| 6,594,511 B2 | 7/2003 | Stone et al. |
| 6,594,512 B2 | 7/2003 | Huang |
| 6,594,513 B1 | 7/2003 | Jobsis et al. |
| 6,597,931 B1 | 7/2003 | Cheng et al. |
| 6,597,933 B2 | 7/2003 | Kiani et al. |
| 6,600,940 B1 | 7/2003 | Fein et al. |
| 6,606,510 B2 | 8/2003 | Swedlow et al. |
| 6,606,511 B1 | 8/2003 | Ali et al. |
| 6,606,512 B2 | 8/2003 | Muz et al. |
| 6,608,562 B1 | 8/2003 | Kimura et al. |
| 6,609,016 B1 | 8/2003 | Lynn |
| 6,615,064 B1 | 9/2003 | Aldrich |
| 6,615,065 B1 | 9/2003 | Barrett et al. |
| 6,618,602 B2 | 9/2003 | Levin et al. |
| 6,622,034 B1 | 9/2003 | Gorski et al. |
| 6,628,975 B1 | 9/2003 | Fein et al. |
| 6,631,281 B1 | 10/2003 | Kästle |
| 6,632,181 B2 | 10/2003 | Flaherty |
| 6,640,116 B2 | 10/2003 | Diab |
| 6,643,530 B2 | 11/2003 | Diab et al. |

| | | |
|---|---|---|
| 6,643,531 B1 | 11/2003 | Katarow |
| 6,647,279 B2 | 11/2003 | Pologe |
| 6,647,280 B2 | 11/2003 | Bahr et al. |
| 6,650,916 B2 | 11/2003 | Cook |
| 6,650,917 B2 | 11/2003 | Diab et al. |
| 6,650,918 B2 | 11/2003 | Terry |
| 6,654,621 B2 | 11/2003 | Palatnik et al. |
| 6,654,622 B1 | 11/2003 | Eberhard et al. |
| 6,654,623 B1 | 11/2003 | Kästle |
| 6,654,624 B2 | 11/2003 | Diab et al. |
| 6,658,276 B2 | 12/2003 | Kianl et al. |
| 6,658,277 B2 | 12/2003 | Wassermann |
| 6,662,033 B2 | 12/2003 | Casciani et al. |
| 6,665,551 B1 | 12/2003 | Suzuki |
| 6,668,182 B2 | 12/2003 | Hubelbank |
| 6,668,183 B2 | 12/2003 | Hicks et al. |
| 6,671,526 B1 | 12/2003 | Aoyagi et al. |
| 6,671,528 B2 | 12/2003 | Steuer et al. |
| 6,671,530 B2 | 12/2003 | Chung et al. |
| 6,671,531 B2 | 12/2003 | Al-Ali et al. |
| 6,671,532 B1 | 12/2003 | Fudge et al. |
| 6,675,031 B1 | 1/2004 | Porges et al. |
| 6,678,543 B2 | 1/2004 | Diab et al. |
| 6,681,126 B2 | 1/2004 | Solenberger |
| 6,681,128 B2 | 1/2004 | Steuer et al. |
| 6,681,454 B2 | 1/2004 | Modgil et al. |
| 6,684,090 B2 | 1/2004 | Ali et al. |
| 6,684,091 B2 | 1/2004 | Parker |
| 6,694,160 B2 | 2/2004 | Chin |
| 6,697,653 B2 | 2/2004 | Hanna |
| 6,697,655 B2 | 2/2004 | Sueppel et al. |
| 6,697,656 B1 | 2/2004 | Al-Ali |
| 6,697,658 B2 | 2/2004 | Al-Ali |
| RE38,476 E | 3/2004 | Diab et al. |
| 6,699,194 B1 | 3/2004 | Diab et al. |
| 6,699,199 B2 | 3/2004 | Asada et al. |
| 6,701,170 B2 | 3/2004 | Stetson |
| 6,702,752 B2 | 3/2004 | Dekker |
| 6,707,257 B2 | 3/2004 | Norris |
| 6,708,049 B1 | 3/2004 | Berson et al. |
| 6,709,402 B2 | 3/2004 | Dekker |
| 6,711,424 B1 | 3/2004 | Fine et al. |
| 6,711,425 B1 | 3/2004 | Reuss |
| 6,712,762 B1 | 3/2004 | Lichter |
| 6,714,803 B1 | 3/2004 | Mortz |
| 6,714,804 B2 | 3/2004 | Al-Ali et al. |
| 6,714,805 B2 | 3/2004 | Jeon et al. |
| RE38,492 E | 4/2004 | Diab et al. |
| 6,719,686 B2 | 4/2004 | Coakley et al. |
| 6,719,705 B2 | 4/2004 | Mills |
| 6,720,734 B2 | 4/2004 | Norris |
| 6,721,584 B2 | 4/2004 | Baker, Jr. et al. |
| 6,721,585 B1 | 4/2004 | Parker |
| 6,725,074 B1 | 4/2004 | Kästle |
| 6,725,075 B2 | 4/2004 | Al-Ali |
| 6,731,962 B1 | 5/2004 | Katarow |
| 6,731,963 B2 | 5/2004 | Finarov et al. |
| 6,731,967 B1 | 5/2004 | Turcott |
| 6,735,459 B2 | 5/2004 | Parker |
| 6,745,060 B2 | 6/2004 | Diab et al. |
| 6,745,061 B1 | 6/2004 | Hicks et al. |
| 6,748,253 B2 | 6/2004 | Norris et al. |
| 6,748,254 B2 | 6/2004 | O'Neil |
| 6,754,515 B1 | 6/2004 | Pologe |
| 6,754,516 B2 | 6/2004 | Mannheimer |
| 6,760,607 B2 | 7/2004 | Al-Ali |
| 6,760,609 B2 | 7/2004 | Jacques |
| 6,760,610 B2 | 7/2004 | Tscupp et al. |
| 6,763,255 B2 | 7/2004 | DeLonzor et al. |
| 6,763,256 B2 | 7/2004 | Kimball et al. |
| 6,770,028 B1 | 8/2004 | Ali et al. |
| 6,771,994 B2 | 8/2004 | Kiani et al. |
| 6,773,397 B2 | 8/2004 | Kelly |
| 6,778,923 B2 | 8/2004 | Norris et al. |
| 6,780,158 B2 | 8/2004 | Yarita |
| 6,791,689 B1 | 9/2004 | Weckstrom |
| 6,792,300 B1 | 9/2004 | Diab et al. |
| 6,801,797 B2 | 10/2004 | Mannheimer et al. |
| 6,801,798 B2 | 10/2004 | Geddes et al. |
| 6,801,799 B2 | 10/2004 | Mendelson |
| 6,801,802 B2 | 10/2004 | Sitzman et al. |
| 6,802,812 B1 | 10/2004 | Walker et al. |
| 6,805,673 B2 | 10/2004 | Dekker |
| 6,810,277 B2 | 10/2004 | Edgar, Jr. et al. |
| 6,813,511 B2 | 11/2004 | Diab et al. |
| 6,816,741 B2 | 11/2004 | Diab |
| 6,819,950 B2 | 11/2004 | Mills |
| 6,822,564 B2 | 11/2004 | Al-Ali |
| 6,825,619 B2 | 11/2004 | Norris |
| 6,826,419 B2 | 11/2004 | Diab et al. |
| 6,829,496 B2 | 12/2004 | Nagai et al. |
| 6,830,711 B2 | 12/2004 | Mills et al. |
| 6,836,679 B2 | 12/2004 | Baker, Jr. et al. |
| 6,839,579 B1 | 1/2005 | Chin |
| 6,839,580 B2 | 1/2005 | Zonios et al. |
| 6,839,582 B2 | 1/2005 | Heckel |
| 6,839,659 B2 | 1/2005 | Tarassenko et al. |
| 6,842,635 B1 | 1/2005 | Parker |
| 6,845,256 B2 | 1/2005 | Chin et al. |
| 6,850,787 B2 | 2/2005 | Weber et al. |
| 6,850,788 B2 | 2/2005 | Al-Ali |
| 6,850,789 B2 | 2/2005 | Schweitzer, Jr. et al. |
| 6,861,639 B2 | 3/2005 | Al-Ali |
| 6,863,652 B2 | 3/2005 | Huang et al. |
| 6,865,407 B2 | 3/2005 | Kimball et al. |
| 6,879,850 B2 | 4/2005 | Kimball |
| 6,882,874 B2 | 4/2005 | Huiku |
| 6,898,452 B2 | 5/2005 | Al-Ali et al. |
| 6,909,912 B2 | 6/2005 | Melker et al. |
| 6,912,413 B2 | 6/2005 | Rantala et al. |
| 6,920,345 B2 | 7/2005 | Al-Ali et al. |
| 6,931,269 B2 | 8/2005 | Terry |
| 6,934,570 B2 | 8/2005 | Kiani et al. |
| 6,941,162 B2 | 9/2005 | Fudge et al. |
| 6,947,781 B2 | 9/2005 | Asada et al. |
| 6,950,687 B2 | 9/2005 | Al-Ali |
| 6,954,664 B2 | 10/2005 | Sweitzer |
| 6,968,221 B2 | 11/2005 | Rosenthal |
| 6,979,812 B2 | 12/2005 | Al-Ali |
| 6,983,178 B2 | 1/2006 | Fine et al. |
| 6,985,763 B2 | 1/2006 | Boas et al. |
| 6,985,764 B2 | 1/2006 | Mason et al. |
| 6,990,426 B2 | 1/2006 | Yoon et al. |
| 6,992,751 B2 | 1/2006 | Okita et al. |
| 6,992,772 B2 | 1/2006 | Block |
| 6,993,371 B2 | 1/2006 | Kiani et al. |
| 6,993,372 B2 | 1/2006 | Fine et al. |
| 6,996,427 B2 | 2/2006 | Ali et al. |
| 7,003,338 B2 | 2/2006 | Weber et al. |
| 7,003,339 B2 | 2/2006 | Diab et al. |
| 7,006,855 B1 | 2/2006 | Sarussi |
| 7,006,856 B2 | 2/2006 | Baker, Jr. et al. |
| 7,016,715 B2 | 3/2006 | Stetson |
| 7,020,507 B2 | 3/2006 | Scharf et al. |
| 7,024,233 B2 | 4/2006 | Ali et al. |
| 7,024,235 B2 | 4/2006 | Melker et al. |
| 7,025,728 B2 | 4/2006 | Ito et al. |
| 7,027,849 B2 | 4/2006 | Al-Ali |
| 7,027,850 B2 | 4/2006 | Wasserman |
| 7,039,449 B2 | 5/2006 | Al-Ali |
| 7,043,289 B2 | 5/2006 | Fine et al. |
| 7,047,055 B2 | 5/2006 | Boas et al. |
| 7,060,035 B2 | 6/2006 | Wasserman |
| 7,062,307 B2 | 6/2006 | Norris et al. |
| 7,067,893 B2 | 6/2006 | Mills et al. |
| 7,072,701 B2 | 7/2006 | Chen et al. |

| | | | | | | |
|---|---|---|---|---|---|---|
| 7,072,702 B2 | 7/2006 | Edgar, Jr. et al. | | 2004/0204865 A1 | 10/2004 | Lee et al. |
| 7,079,880 B2 | 7/2006 | Stetson | | 2004/0210146 A1 | 10/2004 | Diab et al. |
| 7,085,597 B2 | 8/2006 | Fein et al. | | 2004/0215085 A1 | 10/2004 | Schnall |
| 7,096,052 B2 | 8/2006 | Mason et al. | | 2004/0236196 A1 | 11/2004 | Diab et al. |
| 7,096,054 B2 | 8/2006 | Abdul-Hafiz et al. | | 2004/0242976 A1* | 12/2004 | Abreu ........................ 600/315 |
| 7,107,088 B2 | 9/2006 | Aceti | | 2005/0004479 A1 | 1/2005 | Townsend et al. |
| 7,113,815 B2 | 9/2006 | O'Neil et al. | | 2005/0014999 A1 | 1/2005 | Rahe-Meyer |
| 7,123,950 B2 | 10/2006 | Mannheimer | | 2005/0020887 A1 | 1/2005 | Goldberg |
| 7,127,278 B2 | 10/2006 | Melker et al. | | 2005/0033131 A1 | 2/2005 | Chen |
| 7,130,671 B2 | 10/2006 | Baker, Jr. et al. | | 2005/0043599 A1 | 2/2005 | O'Mara |
| 7,132,641 B2 | 11/2006 | Schulz et al. | | 2005/0043600 A1 | 2/2005 | Diab et al. |
| 7,133,711 B2 | 11/2006 | Chernoguz et al. | | 2005/0049468 A1 | 3/2005 | Carlson |
| 7,139,559 B2 | 11/2006 | Kenagy et al. | | 2005/0070773 A1 | 3/2005 | Chin et al. |
| 7,142,901 B2 | 11/2006 | Kiani et al. | | 2005/0070775 A1 | 3/2005 | Chin et al. |
| 7,162,288 B2 | 1/2007 | Nordstrom et al. | | 2005/0075546 A1 | 4/2005 | Samsoondar |
| 7,190,987 B2 | 3/2007 | Lindekugel et al. | | 2005/0075550 A1 | 4/2005 | Lindekugel |
| 7,198,778 B2 | 4/2007 | Achilefu et al. | | 2005/0085704 A1 | 4/2005 | Schulz |
| 7,215,984 B2 | 5/2007 | Diab et al. | | 2005/0090720 A1 | 4/2005 | Wu |
| 7,225,006 B2 | 5/2007 | Al-Ali et al. | | 2005/0101851 A1 | 5/2005 | Chin |
| 7,228,161 B2 | 6/2007 | Chin | | 2005/0197548 A1 | 9/2005 | Dietiker |
| 7,236,811 B2 | 6/2007 | Schmitt et al. | | 2005/0228248 A1 | 10/2005 | Dietiker |
| 7,248,910 B2 | 7/2007 | Li et al. | | 2005/0256386 A1 | 11/2005 | Chan |
| 7,254,433 B2 | 8/2007 | Diab et al. | | 2005/0272986 A1 | 12/2005 | Smith |
| 7,254,434 B2 | 8/2007 | Schulz et al. | | 2005/0277819 A1 | 12/2005 | Kiani et al. |
| 7,280,858 B2 | 10/2007 | Al-Ali et al. | | 2006/0020179 A1 | 1/2006 | Anderson |
| 7,295,866 B2 | 11/2007 | Al-Ali | | 2006/0030764 A1 | 2/2006 | Porges |
| 7,305,262 B2 | 12/2007 | Brodnick et al. | | 2006/0058594 A1 | 3/2006 | Ishizuka et al. |
| 7,315,753 B2 | 1/2008 | Baker, Jr. et al. | | 2006/0074280 A1 | 4/2006 | Martis |
| 2002/0016537 A1 | 2/2002 | Muz et al. | | 2006/0084852 A1 | 4/2006 | Mason et al. |
| 2002/0026109 A1 | 2/2002 | Diab et al. | | 2006/0084878 A1 | 4/2006 | Banet |
| 2002/0028990 A1 | 3/2002 | Sheperd et al. | | 2006/0089547 A1 | 4/2006 | Sarussi |
| 2002/0038078 A1 | 3/2002 | Ito | | 2006/0106294 A1 | 5/2006 | Maser et al. |
| 2002/0038082 A1 | 3/2002 | Chin | | 2006/0122517 A1 | 6/2006 | Banet |
| 2002/0042558 A1 | 4/2002 | Mendelson | | 2006/0129039 A1 | 6/2006 | Lindner |
| 2002/0068859 A1 | 6/2002 | Knopp | | 2006/0155198 A1 | 7/2006 | Schmid |
| 2002/0072681 A1 | 6/2002 | Schnall | | 2006/0173257 A1 | 8/2006 | Nagai |
| 2002/0103423 A1 | 8/2002 | Chin et al. | | 2007/0032710 A1 | 2/2007 | Raridan et al. |
| 2002/0116797 A1 | 8/2002 | Modgil et al. | | 2007/0032712 A1 | 2/2007 | Raridan et al. |
| 2002/0128544 A1 | 9/2002 | Diab et al | | 2007/0032715 A1 | 2/2007 | Eghbal et al. |
| 2002/0133067 A1 | 9/2002 | Jackson, III | | 2007/0060808 A1 | 3/2007 | Hoarau |
| 2002/0156354 A1 | 10/2002 | Larson | | 2007/0073117 A1 | 3/2007 | Raridan |
| 2002/0173706 A1 | 11/2002 | Takatani | | 2007/0073121 A1 | 3/2007 | Hoarau et al. |
| 2002/0190863 A1 | 12/2002 | Lynn | | 2007/0073122 A1 | 3/2007 | Hoarau |
| 2003/0018243 A1 | 1/2003 | Gerhardt et al. | | 2007/0073125 A1 | 3/2007 | Hoarau et al. |
| 2003/0036690 A1 | 2/2003 | Geddes et al. | | 2007/0073126 A1 | 3/2007 | Raridan |
| 2003/0045785 A1 | 3/2003 | Diab et al. | | 2007/0073128 A1 | 3/2007 | Hoarau |
| 2003/0073889 A1 | 4/2003 | Keilbach et al. | | 2007/0078315 A1 | 4/2007 | Kling et al. |
| 2003/0073890 A1 | 4/2003 | Hanna | | 2007/0078316 A1 | 4/2007 | Hoarau |
| 2003/0100840 A1 | 5/2003 | Sugiura et al. | | 2007/0260129 A1 | 11/2007 | Chin |
| 2003/0109775 A1 | 6/2003 | O'Neil et al. | | 2007/0260131 A1 | 11/2007 | Chin |
| 2003/0187337 A1 | 10/2003 | Tarassenko et al. | | 2007/0299328 A1 | 12/2007 | Chin et al. |
| 2003/0197679 A1 | 10/2003 | Ali et al. | | | | |
| 2003/0212316 A1 | 11/2003 | Leiden et al. | | | | |
| 2003/0225323 A1 | 12/2003 | Kiani et al. | | | | |

FOREIGN PATENT DOCUMENTS

| | | |
|---|---|---|
| DE | 3516338 | 11/1986 |
| DE | 37 03 458 | 8/1988 |
| DE | 3938759 | 5/1991 |
| DE | 4210102 | 9/1993 |
| DE | 4423597 | 8/1995 |
| DE | 19632361 | 2/1997 |
| DE | 69123448 | 5/1997 |
| DE | 19703220 | 7/1997 |
| DE | 19640807 | 9/1997 |
| DE | 19647877 | 4/1998 |
| DE | 10030862 | 1/2002 |
| DE | 20318882 | 4/2004 |
| EP | 0127947 | 5/1984 |
| EP | 00194105 | 9/1986 |
| EP | 00204459 | 12/1986 |
| EP | 0 262 779 | 4/1988 |
| EP | 0315040 | 10/1988 |
| EP | 0314331 | 5/1989 |
| EP | 00352923 | 1/1990 |

| | | | |
|---|---|---|---|
| 2004/0006261 A1 | 1/2004 | Swedlow et al. | |
| 2004/0024326 A1 | 2/2004 | Yeo et al. | |
| 2004/0039272 A1 | 2/2004 | Abdul-Hafiz et al. | |
| 2004/0039273 A1 | 2/2004 | Terry | |
| 2004/0054291 A1 | 3/2004 | Schulz et al. | |
| 2004/0068164 A1 | 4/2004 | Diab et al. | |
| 2004/0092805 A1 | 5/2004 | Yarita | |
| 2004/0097797 A1 | 5/2004 | Porges et al. | |
| 2004/0098009 A1 | 5/2004 | Boecker et al. | |
| 2004/0117891 A1 | 6/2004 | Hannula et al. | |
| 2004/0147824 A1 | 7/2004 | Diab et al. | |
| 2004/0158134 A1 | 8/2004 | Diab et al. | |
| 2004/0162472 A1 | 8/2004 | Berson et al. | |
| 2004/0167381 A1 | 8/2004 | Lichter | |
| 2004/0186358 A1 | 9/2004 | Chernow et al. | |
| 2004/0199063 A1 | 10/2004 | O'Neil et al. | |
| 2004/0204637 A1 | 10/2004 | Diab et al. | |
| 2004/0204638 A1 | 10/2004 | Diab et al. | |
| 2004/0204639 A1 | 10/2004 | Casciani et al. | |

| | | | | | |
|---|---|---|---|---|---|
| EP | 0 360 977 | 4/1990 | JP | 11019074 | 1/1999 |
| EP | 00430340 | 6/1991 | JP | 11155841 | 6/1999 |
| EP | 0435 500 | 7/1991 | JP | 11 188019 | 7/1999 |
| EP | 0572684 | 5/1992 | JP | 11244268 | 9/1999 |
| EP | 00497021 | 8/1992 | JP | 20107157 | 4/2000 |
| EP | 0529412 | 8/1992 | JP | 20237170 | 9/2000 |
| EP | 0531631 | 9/1992 | JP | 21245871 | 9/2001 |
| EP | 0566354 | 4/1993 | JP | 22224088 | 8/2002 |
| EP | 0587009 | 8/1993 | JP | 22282242 | 10/2002 |
| EP | 00630203 | 9/1993 | JP | 23153881 | 5/2003 |
| EP | 0 572 684 | 12/1993 | JP | 23153882 | 5/2003 |
| EP | 00615723 | 9/1994 | JP | 23169791 | 6/2003 |
| EP | 00702931 | 3/1996 | JP | 23194714 | 7/2003 |
| EP | 00724860 | 8/1996 | JP | 23210438 | 7/2003 |
| EP | 00793942 | 9/1997 | JP | 23275192 | 9/2003 |
| EP | 0 864 293 | 9/1998 | JP | 23339678 | 12/2003 |
| EP | 01006863 | 10/1998 | JP | 24008572 | 1/2004 |
| EP | 01006864 | 10/1998 | JP | 24089546 | 3/2004 |
| EP | 0875199 | 11/1998 | JP | 24113353 | 4/2004 |
| EP | 00998214 | 12/1998 | JP | 24135854 | 5/2004 |
| EP | 0 898 933 | 3/1999 | JP | 24148069 | 5/2004 |
| EP | 0898933 | 3/1999 | JP | 24148070 | 5/2004 |
| EP | 01332713 | 8/2003 | JP | 24159810 | 6/2004 |
| EP | 01469773 | 8/2003 | JP | 24166775 | 6/2004 |
| EP | 1502529 | 7/2004 | JP | 24194908 | 7/2004 |
| EP | 01491135 | 12/2004 | JP | 24202190 | 7/2004 |
| FR | 2685865 | 1/1992 | JP | 24248819 | 9/2004 |
| GB | 2 259 545 | 3/1993 | JP | 24248820 | 9/2004 |
| JP | 63275325 | 11/1988 | JP | 24261364 | 9/2004 |
| JP | 2013450 | 1/1990 | JP | 24290412 | 10/2004 |
| JP | 2111343 | 4/1990 | JP | 24290544 | 10/2004 |
| JP | 02 191434 | 7/1990 | JP | 24290545 | 10/2004 |
| JP | 2237544 | 9/1990 | JP | 24329406 | 11/2004 |
| JP | 03 173536 | 7/1991 | JP | 24329607 | 11/2004 |
| JP | 3170866 | 7/1991 | JP | 24329928 | 11/2004 |
| JP | 3245042 | 10/1991 | JP | 24337605 | 12/2004 |
| JP | 4174648 | 6/1992 | JP | 24344367 | 12/2004 |
| JP | 4191642 | 7/1992 | JP | 24351107 | 12/2004 |
| JP | 4332536 | 11/1992 | JP | 25034472 | 2/2005 |
| JP | 3124073 | 3/1993 | WO | WO 98/09566 | 10/1989 |
| JP | 5049624 | 3/1993 | WO | WO 90/01293 | 2/1990 |
| JP | 5049625 | 3/1993 | WO | WO 90/04352 | 5/1990 |
| JP | 3115374 | 4/1993 | WO | WO 91/01678 | 2/1991 |
| JP | 05 200031 | 8/1993 | WO | WO 91/11137 | 8/1991 |
| JP | 2005/200031 | 8/1993 | WO | WO 92/00513 | 1/1992 |
| JP | 5212016 | 8/1993 | WO | WO 92/21281 | 12/1992 |
| JP | 06 014906 | 1/1994 | WO | WO 93/09711 | 5/1993 |
| JP | 06014906 | 1/1994 | WO | WO 93/13706 | 7/1993 |
| JP | 6016774 | 3/1994 | WO | WO 93/16629 | 9/1993 |
| JP | 3116255 | 4/1994 | WO | WO 94/03102 | 2/1994 |
| JP | 6029504 | 4/1994 | WO | WO 94/23643 | 10/1994 |
| JP | 6098881 | 4/1994 | WO | WO 95/02358 | 1/1995 |
| JP | 06 154177 | 6/1994 | WO | WO 95/12349 | 5/1995 |
| JP | 6269430 | 9/1994 | WO | WO 95/16970 | 6/1995 |
| JP | 6285048 | 10/1994 | WO | WO 96/13208 | 5/1996 |
| JP | 7001273 | 1/1995 | WO | WO 96/39927 | 12/1996 |
| JP | 7124138 | 5/1995 | WO | WO 97/36536 | 10/1997 |
| JP | 7136150 | 5/1995 | WO | WO 97/36538 | 10/1997 |
| JP | 3116259 | 6/1995 | WO | WO 97/49330 | 12/1997 |
| JP | 3116260 | 6/1995 | WO | WO 98/17174 | 4/1998 |
| JP | 7155311 | 6/1995 | WO | WO 98/18382 | 5/1998 |
| JP | 7155313 | 6/1995 | WO | WO 98/43071 | 10/1998 |
| JP | 3238813 | 7/1995 | WO | WO 98/51212 | 11/1998 |
| JP | 7171139 | 7/1995 | WO | WO 98/57577 | 12/1998 |
| JP | 3134144 | 9/1995 | WO | WO 99/00053 | 1/1999 |
| JP | 7236625 | 9/1995 | WO | WO 99/32030 | 7/1999 |
| JP | 7246191 | 9/1995 | WO | WO 99/47039 | 9/1999 |
| JP | 8256996 | 10/1996 | WO | WO 99/63884 | 12/1999 |
| JP | 9192120 | 7/1997 | WO | WO 00/21438 | 4/2000 |
| JP | 10216113 | 8/1998 | WO | WO 00/28888 | 5/2000 |
| JP | 10216114 | 8/1998 | WO | WO 00/59374 | 10/2000 |
| JP | 10216115 | 8/1998 | WO | WO 01/13790 | 3/2001 |
| JP | 10337282 | 12/1998 | WO | WO 01/16577 | 3/2001 |

| | | |
|---|---|---|
| WO | WO 01/17421 | 3/2001 |
| WO | WO 01/47426 | 3/2001 |
| WO | WO 01/40776 | 6/2001 |
| WO | WO 01/67946 | 9/2001 |
| WO | WO 01/76461 | 10/2001 |
| WO | WO 02/14793 | 2/2002 |
| WO | WO 02/35999 | 5/2002 |
| WO | WO 02/062213 | 8/2002 |
| WO | WO 02/074162 | 9/2002 |
| WO | WO 02/085202 | 10/2002 |
| WO | WO 03/000125 | 1/2003 |
| WO | WO 03/001180 | 1/2003 |
| WO | WO 03/009750 | 2/2003 |
| WO | WO 03/011127 | 2/2003 |
| WO | WO 03/020129 | 3/2003 |
| WO | WO 03/039326 | 5/2003 |
| WO | WO 03/063697 | 8/2003 |
| WO | WO 03/073924 | 9/2003 |
| WO | WO 2004/000114 | 12/2003 |
| WO | WO 2004/006748 | 1/2004 |
| WO | WO 2004/069046 | 8/2004 |
| WO | WO 2004/075746 | 9/2004 |
| WO | WO 2005/002434 | 1/2005 |
| WO | WO 2005/009221 | 2/2005 |
| WO | WO 2005/010567 | 2/2005 |
| WO | WO 2005/010568 | 2/2005 |
| WO | WO 2005/020120 | 3/2005 |
| WO | WO 2005/065540 | 7/2005 |

OTHER PUBLICATIONS

Zahar, N., et al.; "Automatic Feedback Control of Oxygen Therapy Using Pulse Oximetry," *Annual International Conference of the IEEE Engineering in Medicine and Biology Society*, vol. 13, No. 4, pp. 1614-1615 (1991).

Aoyagi, T., et al.; "Analysis of Motion Artifacts in Pulse Oximetry," *Japanese Society ME*, vol. 42, p. 20 (1993) (Article in Japanese—contains English summary of article).

Barreto, A.B., et al.; "Adaptive Cancelation of Motion artifact in Photoplethysmographic Blood Volume Pulse Measurements for Exercise Evaluation," *IEEE-EMBC and CMBEC—Theme 4: Signal Processing*, pp. 983-984 (1995).

Vincente, L.M., et al.; "Adaptive Pre-Processing of Photoplethysmographic Blood Volume Pulse Measurements," pp. 114-117 (1996).

Plummer, John L., et al.; "Identification of Movement Artifact by the Nellcor N-200 and N-3000 Pulse Oximeters," *Journal of clinical Monitoring*, vol. 13, pp. 109-113 (1997).

Barnum, P.T., et al.; "Novel Pulse Oximetry Technology Capable of Reliable Bradycardia Monitoring in the Neonate," *Respiratory Care*, vol. 42, No. 1, p. 1072 (Nov. 1997).

Poets, C. F., et al.; "Detection of movement artifact in recorded pulse oximeter saturation," *Eur. J. Pediatr.*; vol. 156, pp. 808-811 (1997).

Masin, Donald I., et al.; "Fetal Transmission Pulse Oximetry," *Proceedings 19th International Conference IEEE/EMBS*, Oct. 30th-Nov. 2nd, 1997; pp. 2326-2329.

Block, Frank E., Jr., et al.; "Technology evaluation report: Obtaining pulse oximeter signals when the usual probe cannot be used," *International journal of clinical Monitoring and Computing*, vol. 14, pp. 23-28 (1997).

Nijland, Roel, et al.; "Validation of Reflectance Pulse Oximetry: An Evaluation of a new Sensor in Piglets," *Journal of Clinical Monitoring*, vol. 13, pp. 43-49 (1997).

Soto, Denise A.; "A Comparative Study of Pulse Oximeter Measurements: Digit Versus Earlobe," Master of Science Thesis, California State University Dominguez Hills, May 1997, 46 pgs.

Faisst, Karin, et al.; "Intrapartum Reflectance Pulse Oximetry: Effects of Sensor Location and Fixation Duration on Oxygen Saturation Readings," *Journal of Clinical Monitoring*, vol. 13, pp. 299-302 (1997).

Izumi, Akio, et al.; "Accuracy and Utility of a New Reflectance Pulse Oximeter for Fetal Monitoring During Labor," *Journal of Clinical Monitoring*, vol. 13, pp. 103-108 (1997).

Mannheimer, Paul D., et al.; "Wavelength Selection for Low-Saturation Pulse Oximetry," *IEEE Transactions on Biomedical Engineering*, vol. 44, No. 3, pp. 148-158 (Mar. 1997).

"Smaller Product, Tighter Tolerances Pose Dispensing Challenges for Medical Device Manufacturer," *Adhesives Age*, pp. 40-41 (Oct. 1997).

Buschman, J.P., et al.; "Principles and Problems of Calibration of Fetal Oximeters," *Biomedizinische Technik*, vol. 42, pp. 265-266 (1997).

Pickett, John, et al.; "Pulse Oximetry and PPG Measurements in Plastic Surgery," *Proceedings—19th International Conference—IEEE/EMBS*, Chicago, Illinois, Oct. 30-Nov. 2, 1997, pp. 2330-2332.

Leahy, Martin J., et al.; "Sensor Validation in Biomedical Applications," *IFAC Modelling and Control in Biomedical Systems*, Warwick, UK; pp. 221-226 (1997).

Barreto, Armando B., et al.; "Adaptive LMS Delay Measurement in dual Blood Volume Pulse Signals for Non-Invasive Monitoring," *IEEE*, pp. 117-120 (1997).

Crilly, Paul B., et al.; "An Integrated Pulse Oximeter System for Telemedicine Applications," *IEEE Instrumentation and Measurement Technology Conference*, Ottawa, Canada; May 19-21, 1997; pp. 102-104.

DeKock, Marc; "Pulse Oximetry Probe Adhesive Disks: a Potential for Infant Aspiration," *Anesthesiology*, vol. 89, pp. 1603-1604 (1998).

East, Christine E., et al.; "Fetal Oxygen Saturation and Uterine Contractions During Labor," *American Journal of Perinatology*, vol. 15, No. 6, pp. 345-349 (Jun. 1998).

Rhee, Sokwoo, et al.; "The Ring Sensor: a New Ambulatory Wearable Sensor for Twenty-Four Hour Patient Monitoring," *Proceedings of the 20th annual International Conference of the IEEE Engineering in Medicine and Biology Society*, vol. 20, No. 4, pp. 1906-1909 (Oct. 1998).

Yang, Boo-Ho, et al.; "A Twenty-Four Hour Tele-Nursing System Using a Ring Sensor," *Proceedings of the 1998 IEEE International Conference on Robotics & Automation*, Leaven, Belgium, May 1998; pp. 387-392.

König, Volker, et al.; "Reflectance Pulse Oximetry—Principles and Obstetric Application in the Zurich Systems," *Journal of Clinical Monitoring and Computing*, vol. 14, pp. 403-412 (1998).

Nogawa, Masamichi, et al.; "A Novel Hybrid Reflectance Pulse Oximater Sensor with improved Linearity and General Applicability to Various Portions of the Body," *Proceedings of the 20th Annual International Conference of the IEEE Engineering in Medicine and Biology Society*, vol. 20, No. 4, pp. 1858-1861 (1998).

Hayes, Matthew J., et al.; "Quantitative evaluation of photoplethysmographic artifact reduction for pulse oximetry," *SPIE*, vol. 3570, pp. 138-147 (Sep. 1998).

Edrich, Thomas, et al.; "Can the Blood Content of the Tissues be Determined Optically During Pulse Oximetry Without Knowledge of the Oxygen Saturation?—An In-Vitro Investigation," *Proceedings of the 20th Annual International conference of the IEEE Engineering in Medicine and Biology Society*, vol. 20, No. 6, pp. 3072-3075 (1998).

Hayes, Matthew J., et al.; "Artifact reduction in photoplethysmography," *Applied Optics*, vol. 37, No. 31, pp. 7437-7446 (Nov. 1998).

Such, Hans Olaf; "Optoelectronic Non-invasive Vascular Diagnostics Using multiple Wavelength and Imaging Approach," *Dissertation*, (1998).

Lutter, N., et al.; "Comparison of Different Evaluation Methods for a Multi-wavelength Pulse Oximeter," *Biomedizinische Technik*, vol. 43, (1998).

Ferrell, T.L., et al.; "Medical Telesensors," *SPIE*, vol. 3253, pp. 193-198 (1998).

Todd, Bryan, et al.; "The Identification of Peaks in Physiological Signals," *Computers and Biomedical Research*, vol. 32, pp. 322-335 (1999).

Rhee, Sokwoo, et al.; "Design of a Artifact-Free Wearable Plethysmographic Sensor," *Proceedings of the First joint BMES/EMBS Conference*, Oct. 13-16, 1999, Atlanta, Georgia, p. 786.

Rohling, Roman, et al.; "Clinical Investigation of a New Combined Pulse Oximetry and Carbon Dioxide Tension Sensor in Adult Anaesthesia," *Journal o Clinical Monitoring and Computing*, vol. 15; pp. 23-27 (1999).

Ikeda, Kenji, et al.; "Improvement of Photo-Electric Plethysmograph Applying Newly Developed Opto-Electronic Devices," *IEEE Tencon*, pp. 1109-1112 (1999).

Kaestle, S.; "An Algorithm for Reliable Processing of Pulse Oximetry Signals Under strong Noise Conditions," *Dissertation Book*, Lubeck University, Germany (1999).

Seelbach-Göbel, Birgit, et al.; "The prediction of fetal acidosis by means of intrapartum fetal pulse oximetry," *Am J. Obstet. Gynecol.*, vol. 180, No. 1, Part 1, pp. 73-81 (1999).

Yang, Boo-Ho, et al.; "Development of the ring sensor for healthcare automation," *Robotics and Autonomous Systems*, vol. 30, pp. 273-281 (2000).

Rhee, Sokwoo, et al.; "Artifact-Resistant, Power-Efficient Design of Finger-Ring Plethysmographic Sensor—Part I: Design and Analysis," *Proceedings of the 22nd Annual EMBS International Conference*, Chicago, Illinois; Jul. 23-28, 2000; pp. 2792-2795.

Rhee, Sokwoo, et al.; "Artifact-Resistant, Power-Efficient Design of Finger-Ring Plethysmographic Sensor—Part II: Prototyping and Benchmarking," *Proceedings of the 22nd Annual EMBS International Conference*, Chicago, Illinois; Jul. 23-28, 2000; pp. 2796-2799.

Vicenzi, Martin N.; "Transesophageal versus surface pulse oximetry in intensive care unit patients," *Crit. Care Med.*; vol. 28, No. 7, pp. 2268-2270 (2000).

Goldman, Julian M.; "Masimo Signal Extraction Pulse Oximetry," *Journal of Clinical Monitoring and Computing*, vol. 16, pp. 475-483 (2000).

Coetzee, Frans M.; "Noise-Resistant Pulse Oximetry Using a Synthetic Reference Signal," *IEEE Transactions on Biomedical Engineering*, vol. 47, No. 8, Aug. 2000, pp. 1018-1026.

Nilsson, Lena, et al.; "Monitoring of Respiratory Rate in Postoperative Care Using a New Photoplethysmographic Technique," *Journal of Clinical Monitoring and Computing*, vol. 16, pp. 309-315 (2000).

Nijland, Mark J.M., et al.; "Assessment of fetal scalp oxygen saturation determination in the sheep by transmission pulse oximetry," *Am. J. Obstet Gynecol.*, vol. 183, No. 6, pp. 1549-1553 (Dec. 2000).

Edrich, Thomas, et al.; "Pulse Oximetry: An Improved In Vitro Model that Reduces Blood Flow-Related Artifacts," *IEEE Transactions on Biomedical Engineering*, vol. 47, No. 3, pp. 338-343 (Mar. 2000).

Schulz, Christian Eric; "Design of a Pulse Oximetry Sensor Housing Assembly," California State University Master's Thesis, *UMI Dissertation Services*, UMI No. 1401306, (May 2000) 63 pages.

Yao, Jianchu, et al.; "Design of a Plug-and-Play Pulse Oximeter," *Proceedings of the Second Joint EMBS/BMES Conference*, Houston, Texas, Oct. 23-26, 2002; pp. 1752-1753.

Aoyagi, T., et al.; "Pulse Oximeters: background, present and future," *Neonatal Care*, vol. 13, No. 7, pp. 21-27 (2000) (Article in Japanese—contains English summary of article).

Yokota, Nakaura, Takahashi, et al.; "Pilot Model of a Reflectance-Type Pulse Oximeter for Pre-hospital Evaluation," *Journal of the Japanese Society of Emergency Medicine*, Kanto Region, vol. 21, pp. 26-27 (2000) (Article in Japanese—contains English summary of article).

Kaestle, S.; "Determining Artefact Sensitivity of New Pulse Oximeters in Laboratory Using Signals Obtained from Patient," *Biomedizinische Technik*, vol. 45 (2000).

Cubeddu, Rinaldo, et al.; "Portable 8-channel time-resolved optical imager for functional studies of biological tissues," *Photon Migration, Optical Coherence Tomography, and Microscopy, Proceedings of SPIE*, vol. 4431, pp. 260-265 (2001).

Gisiger, P.A., et al.; "OxiCarbo®, a single sensor for the non-invasive measurement of arterial oxygen saturation and $CO_2$ partial pressure at the ear lobe," *Sensor and Actuators*, vol. B-76, pp. 527-530 (2001).

Cysewska-Sobusaik, Anna; "Metrological Problems With noninvasive Transillumination of Living Tissues," *Proceedings of SPIE*, vol. 4515, pp. 15-24 (2001).

Rhee, Sokwoo, et al.; "Artifact-Resistant, Power-Efficient Design of Finger-Ring Plethysmographic Sensor," *IEEE Transactions on Biomedical Engineering*, vol. 48, No. 7, pp. 795-805 (Jul. 2001).

Belal, Suliman Yousef, et al.; "A fuzzy system for detecting distorted plethysmogram pulses in neonates and paediatric patients," *Physiol. Meas.*, vol. 22, pp. 397-412 (2001).

Hayes, Matthew J., et al.; "A New Method for Pulse Oximetry Possessing Inherent Insensitivity to Artifact," *IEEE Transactions on Biomedical Engineering*, vol. 48, No. 4, pp. 452-461 (Apr. 2001).

Gosney, S., et al.; "An alternative position for the pulse oximeter probe," *Anaesthesia*, vol. 56, p. 493 (2001).

Silva, Sonnia Maria Lopez, et al.; "NIR transmittance pulse oximetry system with laser diodes," *Clinical Diagnostic Systems, Proceedings of SPIE*, vol. 4255, pp. 80-87 (2001).

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Earthrowl-Gould, T., et al.; "Chest and abdominal surface motion measurement for continuous monitoring of respiratory function," *Proc. Instn Mech Engrs*, V215, Part H; pp. 515-520 (2001).

Gehring, Harmut, et al.; "The Effects of Motion Artifact and Low Perfusion on the Performance of a New Generation of Pulse Oximeters in Volunteers Undergoing Hypoxemia," *Respiratory Care*, Vo. 47, No. 1, pp. 48-60 (Jan. 2002).

Jopling, Michae W., et al.; "Issues in the Laboratory Evaluation of Pulse Oximeter Performance," *Anesth Analg*, vol. 94, pp. S62-S68 (2002).

Gostt, R., et al.; "Pulse Oximetry Artifact Recognition Algorithm for Computerized Anaesthetic Records," *Journal of Clinical Monitoring and Computing Abstracts*, p. 471 (2002).

Chan, K.W., et al.; "17.3: Adaptive Reduction of Motion Artifact from Photoplethysmographic Recordings using a Variable Step-Size LMS Filter," *IEEE*, pp. 1343-1346 (2002).

Relente, A.R., et al.; "Characterization and Adaptive Filtering of Motion Artifacts in Pulse Oximetry using Accelerometers," *Proceedings of the Second joint EMBS/BMES Conference*, Houston, Texas, Oct. 23-26, 2002; pp. 1769-1770.

Yamaya, Yoshiki, et al.; "Validity of pulse oximetry during maximal exercise in normoxia, hypoxia, and hyperoxia," *J. Appl. Physiol.*, vol. 92, pp. 162-168 (2002).

Lutter, Norbert O:, et al.; "False Alarm Rates of Three Third-Generation Pulse Oximeters in PACU, ICU and IABP Patients," *Anesth Analg*, vol. 94, pp. S69-S75 (2002).

Lutter, N., et al.; "Accuracy of Noninvasive Continuous Blood Pressure; Measurement Utilising the Pulse Transit Time," *Journal of clinical Monitoring and Computing*, vol. 17, Nos. 7-8, pp. 469 (2002).

Liu, Ying, et al.; "Sensor design of new type reflectance pulse oximetry," *Optics in Health Care and Biomedical Optics: Diagnostics and Treatment, Proceedings of SPIE*, vol. 4916, pp. 98-102 (2002).

Kyriacou, Panayiotis A., et al.; "Esophageal Pulse Oximetry Utilizing Reflectance Photoplethysmography," *IEEE Transactions on Biomedical Engineering*, vol. 49, No. 11, pp. 1360-1368 (Nov. 2002).

Kyriacou, P. A., et al.; "Investication of oesophageal photoplethysmographic signals and blood oxygen saturation measurements in cardiothoracic surgery patients," *Physiological Measurement*, vol. 23, No. 3, pp. 533-545 (Aug. 2002).

Tobata, H., et al.; "Study of Ambient Light Affecting Pulse Oximeter Probes," *Ikigaku(Medical Technology)*, vol. 71, No. 10, pp. 475-476 (2002) (Article in Japanese—contains English summary of article).

Irie, A., et al.; "Respiration Monitors—Pulse Oximeters," *Neonatal Care*, vol. 15, No. 12, pp. 78-83 (2002) (Article in Japanese—contains English summary of article).

Koga, I., et al.; "Sigmoid colonic reflectance pulse oximetry and tonometry in a porcine experimental hypoperfusion shock model," *Acta Anaesthesiol Scand*, vol. 46, pp. 1212-1216 (2002).

Shaltis, Phillip, et al.; "Implementation and Validation of a Power-Efficient, High-Speed Modulation Design for Wireless Oxygen Saturation Measurement Systems," *IEEE*, pp. 193-194 (2002).

Warren, Steve, et al.; "Wearable Sensors and Component-Based Design for Home Health Care," *Proceedings of the Second Joint EMBS/BMES Conference*, Houston, Texas; Oct. 23-26, 2002; pp. 1871-1872.

Ericson, M.N., et al.; "In vivo application of a minimally invasive oximetry based perfusion sensor," *Proceedings of the Second Joint EMBS/BMES Conference*, Houston, Texas; Oct. 23-26, 2002, pp. 1789-1790.

Yoon, Gilwon, et al.; Multiple diagnosis based on Photo-plethysmography: hematocrib, SpO2, pulse and respiration, *Optics in Health Care and Biomedical optics: Diagnostics and Treatment; Proceedings of the SPIE*, vol. 4916; pp. 185-188 (2002).

Hase, Kentaro, et al.; "Continuous Measurement of Blood Oxygen Pressure Using a Fiber Optic Sensor Based on Phosphorescense Quenching," *Proceedings of the Second Joint EMBS/BMES Conference*, Houston, Texas; Oct. 23-26, 2002, pp. 1777-1778.

Pothisarn, W., et al.; "A non-invasive hemoglobin measurement based pulse oximetry," *Optics in Health Care and Biomedical Optics: Diagnostics and Treatment; Proceedings of SPIE*, vol. 4916; pp. 498-504 (2002).

Tremper, K.K.; "A Second Generation Technique for Evaluating Accuracy and Reliability of Second Generation Pulse Oximeters," *Journal of Clinical Monitoring and Computing*, vol. 16, pp. 473-474 (2002).

Silva, Sonnia Maria Lopez, et al.; "Near-infrared transmittance pulse oximetry with laser diodes," *Journal of Biomedical Optics*, vol. 8, No. 3, pp. 525-533 (Jul. 2003).

Cyrill, D., et al.; "Adaptive Comb Filter for Quasi-Periodic Physiologic Signals," *Proceedings of the 25th Annual International Conference of the IEEE EMBS*, Cancun, Mexico, Sep. 17-21, 2003; pp. 2439-2442.

Matthews, Nora S. et al.; "An evaluation of pulse oximeters in dogs, cats and horses," *Veterinary Anaesthesia and Analgesia*, vol. 30, pp. 3-14 (2003).

Stetson, Paul F.; "Determining Heart Rate from Noisey Pulse Oximeter Signals Using Fuzzy Logic," *The IEEE International Conference on Fuzzy Systems*, St. Louis, Missouri, May 25-28, 2003; pp. 1053-1058.

Aoyagi, Takuo; "Pulse oximetry: its invention, theory, and future," *Journal of Anesthesia*, vol. 17, pp. 259-266 (2003).

Avidan, A.; "Pulse oximeter ear probe," *Anaesthesia*, vol. 58, pp. 726 (2003).

Lee, C.M., et al.; "Reduction of motion artifacts from photoplethysmographic recordings using wavelet denoising approach," *IEEE EMBS Asian-Pacific Conference on Biomedical Engineering*, Oct. 20-22, 2003; pp. 194-195.

Mendelson, Y., et al.; "Measurement Site and Photodetector Size Considerations in Optimizing Power Consumption of a Wearable Reflectance Pulse Oximeter," *Proceedings of the 25th Annual International conference of the IEEE EMBS*, Cancun, Mexico, Sep. 17-21, 2003; pp. 3016-3019.

Itoh, K., et al.; "Pulse Oximeter," *Toyaku Zasshi* (Toyaku Journal), vol. 25, No. 8, pp. 50-54 (2003) (Article in Japanese—contains English summary of article).

Matsui, A., et al.; "Pulse Oximeter," *Neonatal Care*, vol. 16, No. 3, pp. 38-45 (2003) (Article in Japanese—contains English summary of article).

Nakagawa, M., et al.; "Oxygen Saturation Monitor," *Neonatal Monitoring*, vol. 26, No. 5, pp. 536-539 (2003) (Article in Japanese—contains English summary of article).

Kubota, H., et al.; "Simultaneous Monitoring of PtcCO2 and SpO2 using a Miniature earlobe sensor," *Jinko Kokyo (Aritificial Respiration)*, vol. 20, No. 1, pp. 24-29 (2003).

Lebak, J.W., et al.; "Implementation of a Standards-Based Pulse Oximeter on a Wearable, Embedded Platform," *Proceeding of the 25th Annual International Conference of the IEEE EMBS*, Cancun, Mexico, Sep. 17-21, 2003; pp. 3196-3198.

Nagl, L., et al.; "Wearable Sensor System for Wireless State-of-Health Determination in Cattle," *Proceeding of the 25th Annual International Conference of the IEEE EMBS*, Cancun, Mexico, Sep. 17-21, 2003; pp. 3012-3015.

Östmark, Åke, et al.; "Mobile Medical Applications Made Feasible Through Use of EIS Platforms," *IMTC—Instrumentation and Measurement Technology Conference*, Vail, Colorado; May 20-22, 2003; pp. 292-295.

Warren, Steve, et al.; "A Distributed Infrastructure for Veterinary Telemedicine," *Proceedings of the 25th Annual International Conference of the IEEE EMBS*, Cancun, Mexico; Sep. 17-21, 2003; pp. 1394-1397.

Pujary, C., et al.; "Photodetector Size Considerations in the Design of a Noninvasive Reflectance Pulse Oximeter for Telemedicine Applications," *IEEE*, pp. 148-149 (2003).

A. Johansson; "Neural network for photoplethysmographic respiratory rate monitoring," *Medical & Biological Engineering & Computing*, vol. 41, pp. 242-248 (2003).

Reuss, James L.; "Factors Influencing Fetal Pulse Oximetry Performance," *Journal of clinical Monitoring and Computing*, vol. 18, pp. 13-14 (2004).

Mannheimer, Paul D., et al.; "The influence of Larger Subcutaneous Blood Vessels on Pulse Oximetry," *Journal of clinical Monitoring and Computing*, vol. 18, pp. 179-188 (2004).

Wendelken, Suzanne, et al.; "The Feasibility of Using a Forehead Reflectance Pulse Oximeter for Automated Remote Triage," *IEEE*, pp. 180-181 (2004).

Lopez-Silva, S.M., et al.; "Transmittance Photoplethysmography and Pulse Oximetry With Near Infrared Laser Diodes," *IMTC 2004—Instrumentation and Measurement Technology Conference*, Como, Italy, May 18-20, 2004; pp. 718-723.

Sugino, Shigekzau, et al.; "Forehead is as sensitive as finger pulse oximetry during general anesthesia," *Can J. Anesth.; General Anesthesia*, vol. 51, No. 5; pp. 432-436 (2004).

Addison, Paul S., et al.; "A novel time-frequency-based 3D Lissajous figure method and its application to the determination of oxygen saturation from the photoplethysmogram," *Institute of Physic Publishing, Meas. Sci. Technol.*, vol. 15, pp. L15-L18 (2004).

Jovanov, E., et al.; "Reconfigurable intelligent Sensors for Health Monitoring: A case Study of Pulse Oximeter Sensor," *Proceedings o the 26th Annual International conference of the IEEE EMBS*, San Francisco, California, Sep. 1-5, 2004, pp. 4759-4762.

Kocher, Serge, et al.; "Performance of a Digital $PCO_2/SPO_2$ Ear Sensor," *Journal of Clinical Monitoring and Computing*, vol. 18, pp. 75-59 (2004).

Yao, Jianchu, et al.; "A Novel Algorithm to Separate Motion Artifacts from Photoplethysmographic Signals Obtained With a Reflectance Pulse Oximeter," *Proceedings of the 26th Annual International conference of the IEEE EMBS*, San Francisco, California, Sep. 1-5, 2004; pp. 2153-2156.

Nuhr, M., et al.: "Forehead $SpO_2$ monitoring compared to finger $SpO_2$ recording in emergency transport," *Anaesthesia*, vol. 59, pp. 390-393 (2004).

Johnston, William S., et al.; "Effects of Motion Artifacts on helmet-Mounted Pulse Oximeter Sensors," 2 pgs. (2004).

Branche, Paul C., et al.; "Measurement Reproducibility and Sensor Placement Considerations in Designing a Wearable Pulse Oximeter for Military Applications," 2 pgs. (2004).

Heuss, Ludwig T., et al.; "Combined Pulse Oximetry / Cutaneous Carbon dioxide Tension Monitoring During Colonoscopies: Pilot study with a Smart Ear Clip," *Digestion*, vol. 70, pp. 152-158 (2004).

Matsuzawa, Y., et al.; "Pulse Oximeter," *Home Care Medicine*, pp. 42-45 (Jul. 2004); (Article in Japanese—contains English summary of article).

Crespi, F., et al.; "Near infrared oxymeter prototype for non-invasive analysis of rat brain oxygeneration," *Optical Sensing, Proceedings of SPIE*, vol. 5459, pp. 38-45 (2004).

Johnston, W.S., et al.; "Extracting Breathing Rate Infromation from a Wearable Reflectance Pulse Oximeter Sensor," *Proceedings of the 26th Annual International conference of the IEEE EMBS*, San Francisco, California; Sep. 1-5, 2004; pp. 5388-5391.

Spigulis, Janis, et al.; "Optical multi-channel sensing of skin blood pulsations," *Optical Sensing, Proceedings of SPIE*, vol. 5459, pp. 46-53 (2004).

Yan, Yong-sheng, et al.; "Reduction of motion artifact in pulse oximetry by smoothed pseudo Wigner-Ville distribution," *Journal of NeuroEngineering and Rehabilitation*, vol. 2, No. 3 (9 pages) (Mar. 2005).

Urquhart, C., et al.; "Ear probe pulse oximeters and neonates," *Anaesthesia*, vol. 60, p. 294 (2005).

J. Hayoz, et al.; "World's First Combined digital Pulse Oximetry Pulse Oximetry and Carbon Dioxide Tension Ear Sensor", *Abstracts*, A6, p. S103. (undated).

J. Huang, et al.; "Low Power Motion Tolerant Pulse Oximetry," *Abstracts*, A7, p. S103. (undated).

P. Lang, et al.; "Signal Identification and Quality Indicator™ for Motion Resistant Pulse Oximetry," *Abstracts*, A10, p. S105. (undated).

Hamilton, Patrick S., et al.; "Effect of Adaptive Motion-Artifact Reduction on QRS Detection," *Biomedical Instrumentation & Technology*, pp. 197-202 (undated).

Kim, J.M., et al.; "Signal Processing Using Fourier & Wavelet Transform," pp. II-310-II-311 (undated).

Lee, C.M., et al.; "Reduction of Motion Artifacts from Photoplethysmographic Records Using a Wavelet Denoising Approach," *IEEE*, pp. 194-195 (undated).

Nogawa, Masamichi, et al.; "A New Hybrid Reflectance Optical Pulse Oximetry Sensor for Lower Oxygen Saturation Measurement and for Broader Clinical Application," *SPIE*, vol. 2976, pp. 78-87 (undated).

Odagiri, Y.; "Pulse Wave Measuring Device," *Micromechatronics*, vol. 42, No. 3, pp. 6-11 (undated) (Article in Japanese—contains English summary of article).

Yamazaki, Nakaji, et al.; "Motion Artifact Resistant Pulse Oximeter (Durapulse PA 2100)," *Journal of Oral Cavity Medicine*, vol. 69, No. 4, pp. 53 (date unknown) (Article in Japanese—contains English summary of article).

\* cited by examiner

MEDICAL SENSOR AND TECHNIQUE FOR USING THE SAME

BACKGROUND OF THE INVENTION

1. Field of the Invention

The present invention relates generally to medical devices and, more particularly, to sensors used for sensing physiological parameters of a patient.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such physiological characteristics. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heartbeat of a patient. In fact, the "pulse" in pulse oximetry refers to the time varying amount of arterial blood in the tissue during each cardiac cycle.

Pulse oximeters typically utilize a non-invasive sensor that transmits light through a patient's tissue and that photoelectrically detects the absorption and/or scattering of the transmitted light in such tissue. One or more of the above physiological characteristics may then be calculated based upon the amount of light absorbed or scattered. More specifically, the light passed through the tissue is typically selected to be of one or more wavelengths that may be absorbed or scattered by the blood in an amount correlative to the amount of the blood constituent present in the blood. The amount of light absorbed and/or scattered may then be used to estimate the amount of blood constituent in the tissue using various algorithms.

Conventional pulse oximetry sensors are either disposable or reusable. Disposable sensors are typically simple bandage-type structures attached to the patient with adhesive materials, providing a contact between the patient's skin and the sensor components. However, their flexible nature renders them susceptible to motion artifacts caused by mechanical deformation of the sensor. Additionally, the adhesives used to secure the bandage sensors are generally designed for a single application, as they tend to lose adhesive strength when removed from the tissue for repositioning of the sensor. The sensor adhesives may also not adhere well to tissue that has blood or sweat on the surface.

Reusable sensors are often semi-rigid or rigid clip-type devices with three-dimensional geometry and moving parts. The clips generally affix the sensor components to a patient's tissue with spring-loaded hinges designed to hold the sensor in place after application. Clip-style pulse oximeter sensors are used repeatedly and, typically, on more than one patient. Therefore, over the life of the sensor, detritus and other bio-debris (sloughed off skin cells, dried fluids, dirt, and so forth) may accumulate on the surface of the sensor or in crevices and cavities of the sensor, after repeated uses. Thus, a thorough cleaning of a clip-style sensor may involve disassembly of the sensor and individual cleaning of the disassembled parts, or may involve careful cleaning using utensils capable of reaching into cavities or crevices of the sensor. Such cleaning is labor intensive and may be impractical in a typical hospital or clinic environment. Clip-style sensors with hinges or complex moving parts may also be more expensive to manufacture and transport. For example, a clip-style sensor with a complex structure and moving parts may require extra protection during shipping. Additionally, the complex structure of a clip-style sensor prevents easy stacking of multiple sensors in a single packaging system.

Although the clip-style sensor design provides a familiar and easy-to-use device for affixing the sensor components to a patient, the structure of the clip provides cleaning, manufacturing, and packaging challenges. It would be desirable to provide a clip-style pulse oximetry sensor that is easy to manufacture and use and that also provides suitable tissue contacting strength without complex mechanical components.

SUMMARY

Certain aspects commensurate in scope with the originally claimed invention are set forth below. It should be understood that these aspects are presented merely to provide the reader with a brief summary of certain forms that the invention might take and that these aspects are not intended to limit the scope of the invention. Indeed, the invention may encompass a variety of aspects that may not be set forth below.

There is provided a sensor that includes: a sensor body comprising a material with shape memory, wherein the sensor body is adapted to assume a substantially curved configuration in the absence of a deforming force; and at least one sensing element disposed on the sensor body.

There is also provided a pulse oximetry system that includes: a pulse oximetry monitor; and a pulse oximetry sensor adapted to be operatively coupled to the monitor, the sensor including: a sensor body comprising a material with shape memory, wherein the sensor body is adapted to assume a substantially curved configuration in the absence of a deforming force; and at least one sensing element disposed on the sensor body.

There is also provided a sensor packaging system that includes: a protective package having an interior to hold at least one sensor in its interior; and at least one sensor having at least one sensing element, whereby the sensor includes a material having shape memory and whereby the sensor is restrained in a substantially planar position. The sensor is adapted to be curved in the absence of a deforming force.

There is also provided a method for packaging a sensor that includes: providing a substantially curved sensor body comprising at least one sensing element and a material with shape memory; deforming the sensor body into a substantially flat position; restraining the sensor body in the substantially flat position with a removable restraining element; and packaging the sensor in a packaging container.

There is also provided a method of manufacturing a sensor that includes: providing a sensor body comprising a material with shape memory, wherein the sensor body is adapted to assume a substantially curved configuration in the absence of a deforming force; and providing at least one sensing element disposed on the sensor body.

BRIEF DESCRIPTION OF THE DRAWINGS

Advantages of the invention may become apparent upon reading the following detailed description and upon reference to the drawings in which.

DETAILED DESCRIPTION OF SPECIFIC EMBODIMENTS

Figure 1A:
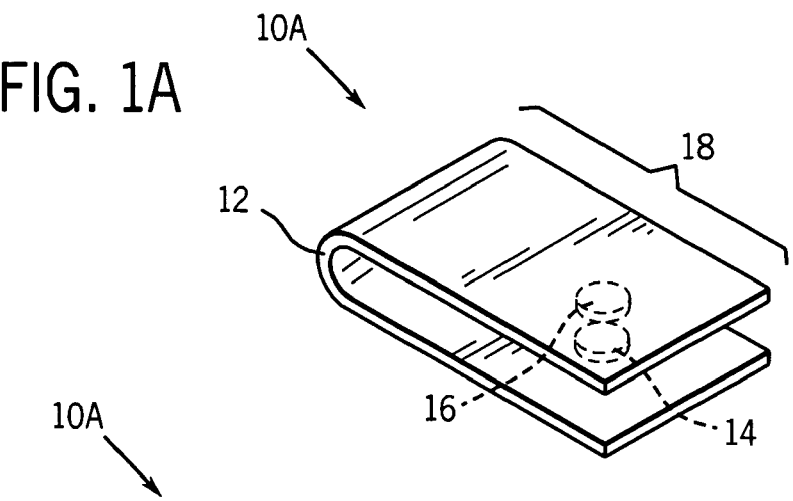
FIG. 1A illustrates an embodiment of an exemplary clip-style pulse oximetry sensor with a flat spring in the memory configuration according to the present invention.

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

The present techniques provide an improved medical sensor for pulse oximetry or other spectrophotometric uses. The sensor is constructed from a material with a shape memory of a curvature or a bend, such that the material will tend to return to its "memorized" shape if deformed therefrom. Thus, a sensor so constructed may have fewer parts, as the spring force of the sensor is provided by the shape memory material. Generally, such a sensor may provide certain advantages for storage or shipping. For example, when a sensor according to the present techniques is packaged for shipping, it may be flattened and restrained in a planar position that allows the sensors to be packaged efficiently for transport. Because the sensor is made of a material that has memory, when the restraints are removed from the sensor, the sensor will revert to a curved shape that provides sufficient spring force to affix the sensor to the patient.

Sensors for pulse oximetry or other spectrophotometric uses are typically placed on a patient in a location that is normally perfused with arterial blood to facilitate measurement of the desired blood characteristics, such as arterial oxygen saturation measurement ($SpO_2$). Clip-style sensors are often used on patient digits, earlobes, or nose bridges. Such sensors rely on a spring force to hold the sensor in place.

For the exemplary sensors described below, the spring force is provided by a shape memory material. Materials which possess the characteristic of having shape memory are well known, and include certain metal alloys, plastics, and polymers. Any suitable shape-memory materials may be used, such as a nickel-titanium alloy (NiTi). One such NiTi alloy is manufactured, for example, by Shape Memory Applications, Inc., Santa Clara, Calif. A pulse oximetry sensor made of such materials can be moved between an original memory configuration to a deformed configuration, and the sensor 10 may revert to the original memory configuration under specified conditions. A sensor 10 constructed from a shape memory material may be converted from the memory configuration to a deformed configuration upon receiving a certain stimulus, such as temperature change, electrical stimulation, or mechanical force. The sensor 10 will be able to recover from the deformed configuration to resume the original memory configuration upon removal of the deforming stimulus. This tendency towards reversion to the memory configuration provides the spring force to affix the pulse oximetry sensor 10 to a patient.

In one such specific example, the sensor may be made from a shape memory material that may undergo a phase transformation during application of a pure mechanical load. In general, metallic shape-memory alloys, such as NiTi, CuZnAl, and CuAlNi alloys, exhibit the property of solid-to-solid phase transitions. Specifically, shape-memory material is able to undergo a transformation from a solid austenite state to a solid martensite state. The austenite state generally exists at higher temperatures and is associated with more order among the atoms of the alloy, while the more atomically disordered martensite state exists at lower temperatures.

A shape memory is "fixed" in a shape memory material by holding the material in its desired memory shape while heating it to a temperature beyond the transformation temperature range that marks the phase change between the austenite state and the martensite state. For example, certain NiTi alloys are heated to approximately 500° C. to achieve a state in which a memory configuration can be fixed. In such a state, each titanium atom is surrounded by a cube of nickel atoms. When the material is cooled through a transformation temperature range after heating, the atoms adopt the more disordered martensite state. Transformation temperatures can vary widely depending on the composition of the alloy, and may range from –195° C. to 100° C.

Although shape memory materials can undergo temperature-induced shape recovery, they also may exhibit a pseudo-elastic shape recovery without a change in temperature under mechanical loads. As the transformation between austenite and martensite is an atomic rearrangement, mechanical loads may also trigger the atomic changes that lead to the solid-to-solid phase transformation. When the load is released the shape memory material in the martensite state begins to transform back to austenite. Generally, a sensor made from shape memory materials described herein experiences substantially complete shape recovery at temperatures associated with normal use, such as room temperatures in the range of 18° C.-25° C.

Figure 1B:
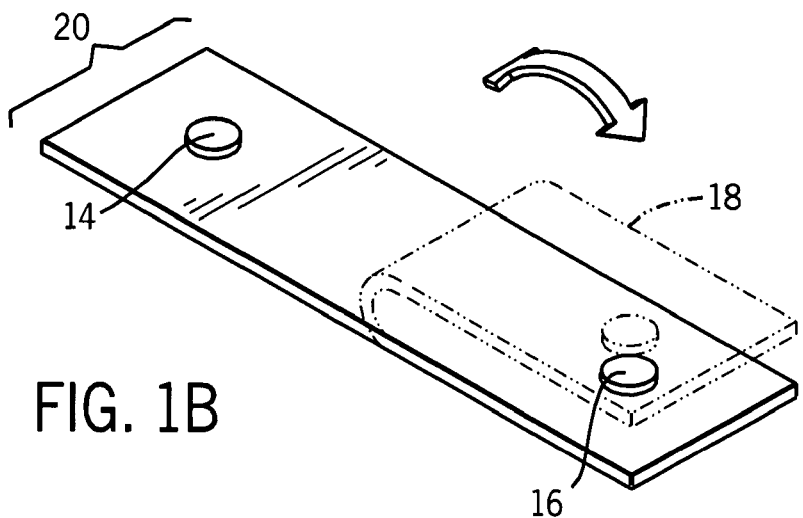
FIG. 1B illustrates the pulse oximetry sensor of FIG. 1A in the planar configuration due to a deforming stress.
Figure 1C:
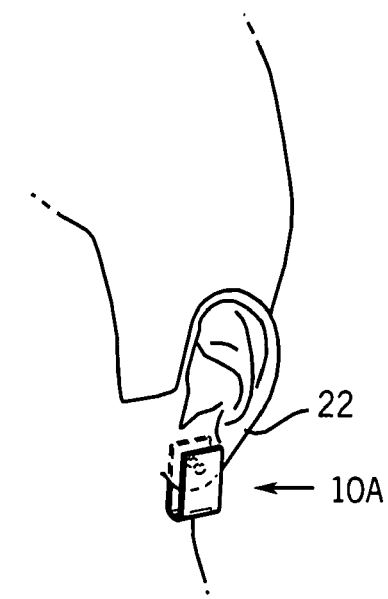
FIG. 1C illustrates the pulse oximetry sensor of FIG. 1A applied to a patient earlobe.

Clip-style pulse oximetry sensors that are constructed from materials with shape memory may take a variety of forms. For example, FIGS. 1A-C illustrate a sensor 10A adapted for use on a patient's earlobe. The sensor 10A has a flat spring 12 that is constructed at least in part from a shape memory material. The flat spring 12 is adapted to house an emitter 14 and a detector 16. One with skill in the art is aware that the emitter 14 and the detector 16 may include wires (not shown) or other electrical connections that allow the sensor 10A to communicate with a monitor, as discussed in more detail herein. The sensor 10A may be adapted to include grooves or channels for wires connected to the emitter 14 and the detector 16, such that the wires may be embedded in the sensor body. In other embodiments, wires connected to the emitter 14 and the detector 16 may run along the surface of the sensor body, either on a tissue-contacting surface or a surface that does not contact the tissue during use.

The sensor 10A shown in FIG. 1A is in its memory configuration 18 (e.g., its undeformed austenitic state). The flat spring 12 is shaped such that the radius of curvature of the flat spring 12 is sufficient to provide suitable spring force to attach the sensor 10A to a patient's earlobe. The flat spring 12 in its memory configuration 18 can be readily straightened by the application of manual force. When such force is applied to the flat spring 12, at least part of the austenitic phase is converted to the martensitic phase so long as the force is maintained. FIG. 1B illustrates a perspective view of the planar configuration 20 of the sensor 10A after the application of a deforming force. As soon as the deforming force is removed, the sensor 10A then returns pseudoelastically to its memory configuration 18, with part of the martensitic phase converting back to the austenitic phase. As shown in FIG. 1C, the sensor recovers from the planar configuration 20 enough to provide suitable spring force to attach the sensor to the patient's earlobe 22.

It is contemplated that the radius of curvature of the sensor 10A in the memory configuration 18 may be adjusted to provide customized pressure to the patient's earlobe. In certain embodiments, the spring force that the flat spring 12 exerts on the earlobe provides sufficient pressure so that the pressure exceeds the typical venous pressure of a patient, but does not exceed the diastolic arterial pressure. As the pulse oximetry measurements are related to arterial blood oxygen saturation and pulsation, and not venous blood pulsation, reducing the effect of the venous component in the tissue may enhance the sensitivity of the sensor to variations in the arterial blood signal. Thus, the sensor 10A may apply a pressure greater than the venous pressure to squeeze excess pooled venous blood from the optically probed tissue. Yet, since the pressure applied by the sensor 10A is designed to be less than the arterial pressure, the application of pressure to the tissue does not interfere with the arterial pulse signal. Typical venous pressure, diastolic arterial pressure, and systolic arterial pressure are less than 10-35 mmHg, 80 mmHg, and 120 mmHg, respectively. Accordingly, in certain embodiments, the sensor may be adjusted to overcome an average venous pressure of 15-35 mmHg. However, venous pressures may vary because of the location of the vascular bed and the patient's condition. For example, low arterial diastolic blood pressure (about 30 mmHg) may occur in sick patients. In such embodiments, the sensor 10A removes most of the venous pooling with by applying sufficient pressure to overcome light to moderate venous pressure (about 15 mmHg).

Figure 2:
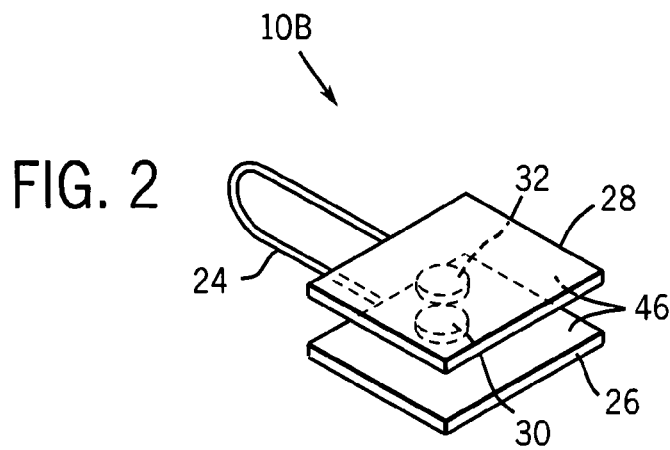
FIG. 2 illustrates an embodiment of an exemplary pulse oximetry sensor in the memory configuration with a shape memory wire.

In certain embodiments, it may be advantageous, e.g., for reasons related to expense or design, to use a limited amount of shape memory material. Hence, the shape memory material may be in a form in which it is reduced in bulk, such as the form of a strip, a mesh, a tube, a strap, or a wire. As one example, FIG. 2 illustrates a sensor 10B according to the present technique in which a shape memory strap 24 connects a first portion 26 and a second portion 28. The first portion 26 and the second portion 28 house an emitter 30 and a detector 32, which are disposed on the tissue-contacting sides 46 of the first portion 26 and the second portion 28, respectively. The first portion 26 and the second portion 28 may be constructed from any suitable rigid or semi-rigid material, such as rubber, metal, or plastic. In one embodiment (not shown) the first portion 26 and the second portion 28 may have foam pads (not shown) disposed on their tissue-contacting sides 46 to provide a more comfortable contact with the patient's skin. The sensor 10B as described above may be advantageous for application to the bridge of a patient's nose or a patient's earlobe. The shape memory strap 24 is sufficiently flexible to fit over a wide variety of sizes and shapes of nose bridges or earlobes, but has sufficient spring force due to its pseudoelastic properties to ensure a secure fit. Additionally, the shape memory strap 24 may be thin enough to fit comfortably over the bridge of the nose without obscuring the patient's vision, particularly as the sensor 10B does not have protruding handles.

Figure 3A:
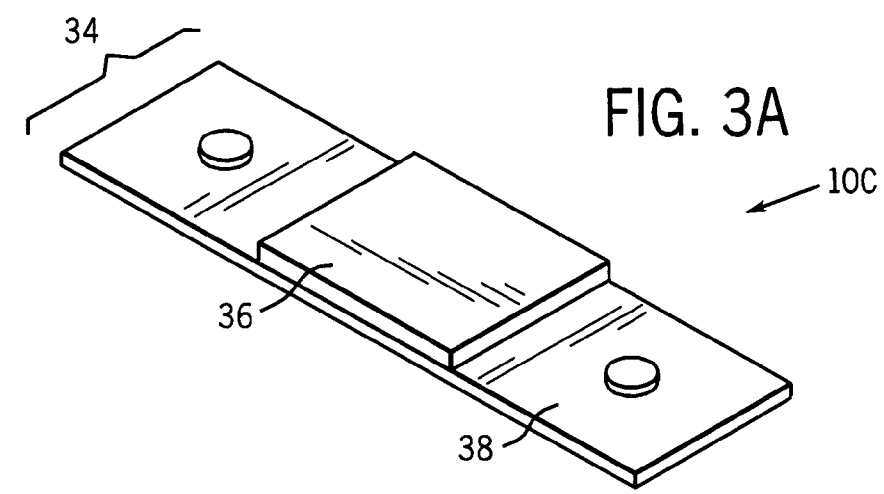
FIG. 3A illustrates a perspective view of an exemplary pulse oximetry sensor in the planar configuration with a breakable restraining element according to the present invention.
Figure 3B:
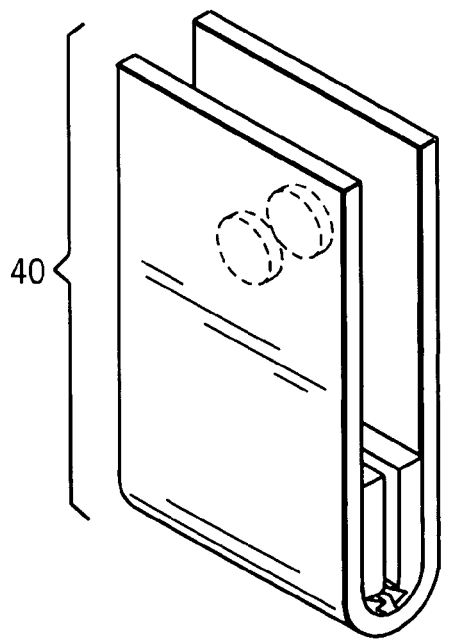
FIG. 3B illustrates the pulse oximetry sensor of FIG. 3A in the memory configuration after the restraining element has been broken.

As discussed above, an advantage conferred by the present techniques is that a sensor 10 may be retained in a substantially planar configuration that allows for ease of storing and packaging. Although the package in which a sensor is placed may confer the mechanical force to retain the sensor in its deformed configuration, a sensor may include a component that performs this function instead. Turning to FIGS. 3A-B, an exemplary embodiment is depicted in which a sensor 10C includes such a restraining element. As shown in FIG. 3A, the restraining element 36 suitable to restrain the sensor 10C in a substantially flat configuration may be breakable or removable. For the former use, the restraining element 36 may be constructed from brittle ceramic or plastic. The breakable restraining element 36 may be adhesively or otherwise disposed in a region of the sensor 10C that exhibits the greatest amount of curvature when in the undeformed memory configuration. As depicted, the breakable restraining element 36 is disposed on the tissue-contacting side 38 of the sensor 10C in the interior of the curve, although it should be appreciated that the restraining element 36 may be disposed on the other side instead. The breakable restraining element 36 has sufficient strength to overcome the tendency of the sensor to revert to the undeformed memory configuration 40, as depicted in FIG. 3B. Nevertheless, the breakable restraining element 36 may also be sufficiently brittle such that it may be easily broken by hand by a healthcare worker prior to application of the sensor 10C. FIG. 3B shows the sensor 10C in the undeformed memory configuration 40 after breaking of the breakable restraining element 36. In other embodiments (not shown), the breakable restraining element 36 may be scored, which may allow it to be broken more easily by the user.

Figure 4:
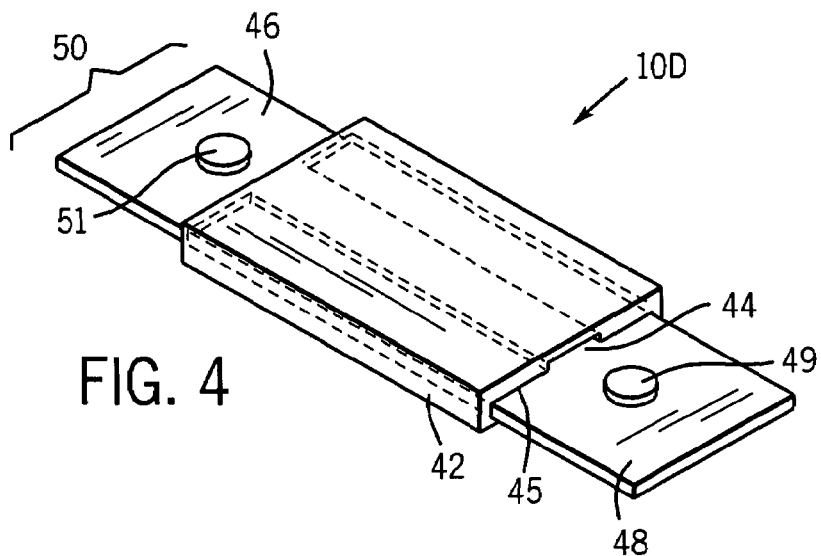
FIG. 4 illustrates a perspective view of an exemplary pulse oximetry sensor with a sliding restraining element according to the present invention.

In other embodiments, it may be appropriate to employ a restraining element that does not break during the removal process and is, thus, reusable. FIG. 4 depicts a sensor 10D made from a shape memory material with a sleeve-like restraining element 42 with at least one opening 44 having a slot 45, sized to fit over a first end 46 or a second end 48 of the sensor 10D. The slot 45 is configured such that it fits the sensor 10D snugly near the edges of the sensor to prevent curvature of the memory material. The opening 44 is arranged to correspond with the emitter 49 and the detector 51, such that when the sleeve-like restraining element slides over the first end 46 or the second end 48, the opening allows the emitter 49 or the detector 51 to slide through. The sensor 10D is depicted in the planar configuration 50, and the memory configuration (not shown) is substantially U-shaped. The opening 44 is configured to allow easy removal, but is snug enough to prevent curving of the sensor 10D to partially revert to the U-shaped memory configuration. The sleeve-like restraining element 42 serves to hold the sensor 10D in the planar configuration 50 until the sleeve-like restraining element 42 is removed. The sleeve-like restraining element 42 may be removed by sliding it off the first end 40 or the second end 42 of the sensor 10D. The sleeve-like restraining element 42 may be made from any suitable material that serves to overcome the tendency of the sensor 10D to revert to the U-shaped memory configuration, such as metal or plastic. After the sensor 10D is removed from the patient, the sleeve-like restraining element 42 can be reapplied to the sensor 10D. Thus, the sensor 10D can be returned to the planar configuration 50 for storage.

Figure 5:
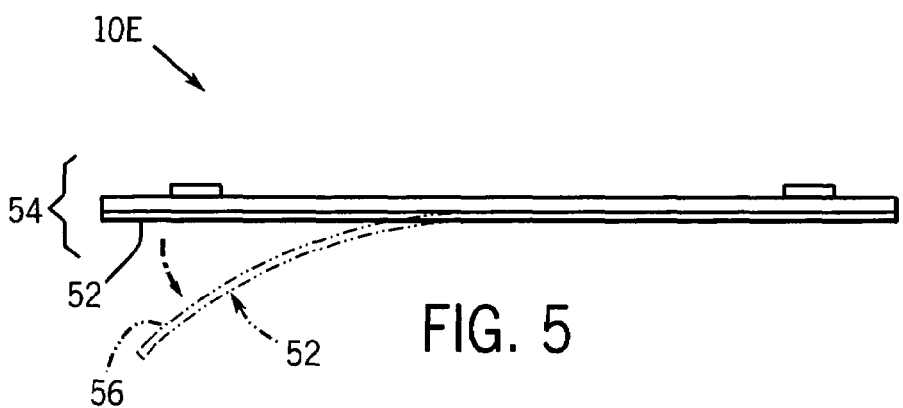
FIG. 5 illustrates a perspective view of an exemplary pulse oximetry sensor with an adhesive restraining element according to the present invention.

In other embodiments, it may be less costly to manufacture a sensor with a disposable adhesive restraining element. As one example, a sensor 10E with a peelable adhesive layer 52 that keeps the sensor in the substantially planar configuration 54 is illustrated in FIG. 5. The peelable adhesive layer 52 may be paper, plastic, polyester, woven fabric, or any other suitable material that serves to overcome the tendency of the sensor 10E to revert to its U-shaped memory configuration (not shown). The peelable adhesive layer 52 is coated with an adhesive on the sensor contacting side 56 and is disposed on the surface of the sensor 10E that does not contact the tissue during normal use. The peelable adhesive layer 52 may be removed by a healthcare worker prior to application of the sensor 10E to a patient.

In one embodiment (not shown), an adhesive material may be applied to the tissue-contacting side of the sensor 10E to facilitate securing the sensor to the patient. The use of an adhesive material improves the contact of the sensor to the patient and limits its susceptibility to motion artifacts. Because the sensor 10E is stored in a substantially planar configuration 54, the adhesive regions of the sensor 10E may be less likely to come into contact with one another than if the sensor 10E were in the U-shaped memory configuration.

Figure 6:
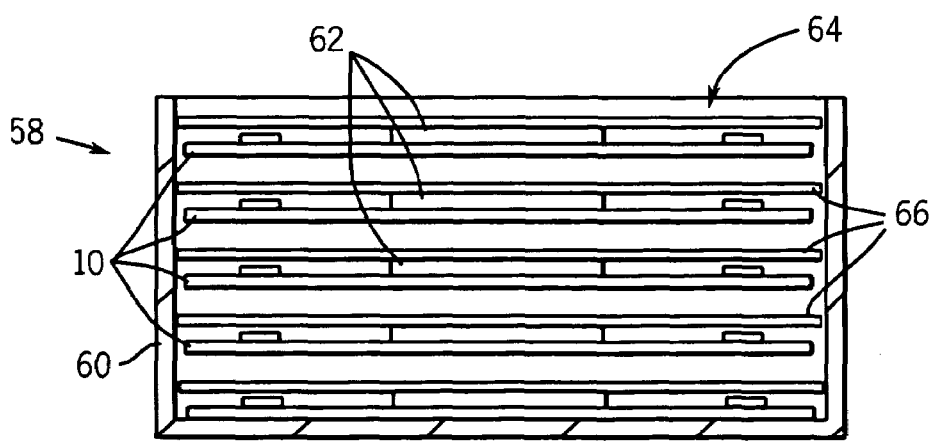
FIG. 6 illustrates a cross sectional view of an exemplary pulse oximetry sensor packaging system with multiple pulse oximetry sensors according to the present invention.

The present techniques provide sensors that may be more efficiently packaged and shipped due to their generally planar configuration. Accordingly, FIG. 6 illustrates an exemplary packaging system 58 for storing and transporting a pulse oximetry sensor (generically identified here as a sensor 10) that includes at least one pulse oximetry sensor 10, a protective package 60, and restraining elements 62. The restraining elements 62 hold the respective sensors 10 in the planar configuration. The restraining element 62 may be attached to the sensor 10 as described above. For example, the restraining element may be any of the restraining elements described herein (e.g. breakable restraining element 36, sleeve-like restraining element 42, peelable adhesive layer 52). Alternatively, the restraining element may be incorporated into the packaging system 58. For example, the packaging system may include slots (not shown) that the sensors 10 may slide into and that restrain the sensors 10 in the planar configuration. When the sensors 10 are removed, they will revert to a U-shaped configuration. As shown, the packaging system 58 may include multiple stacked sensors 10 in the interior 64 of the protective package 60. Thin protective sheets 66 may separate the stacked sensors 10. The thin protective sheets 66 may be a relatively rigid material, such as plastic, that may provide the straightening force to the sensors 10. The planar configuration of the sensors 10 allows more convenient stacking as compared to a typical U-shaped clip-style sensor. The stacked sensors 10 in the planar configuration also occupy less space, and thus a larger number of sensors may be packaged in a packaging system relative to U-shaped sensors. Additionally, since the sensors 10 have no moving parts, the amount of protective packaging used for shipping may be minimal.

Figure 7:
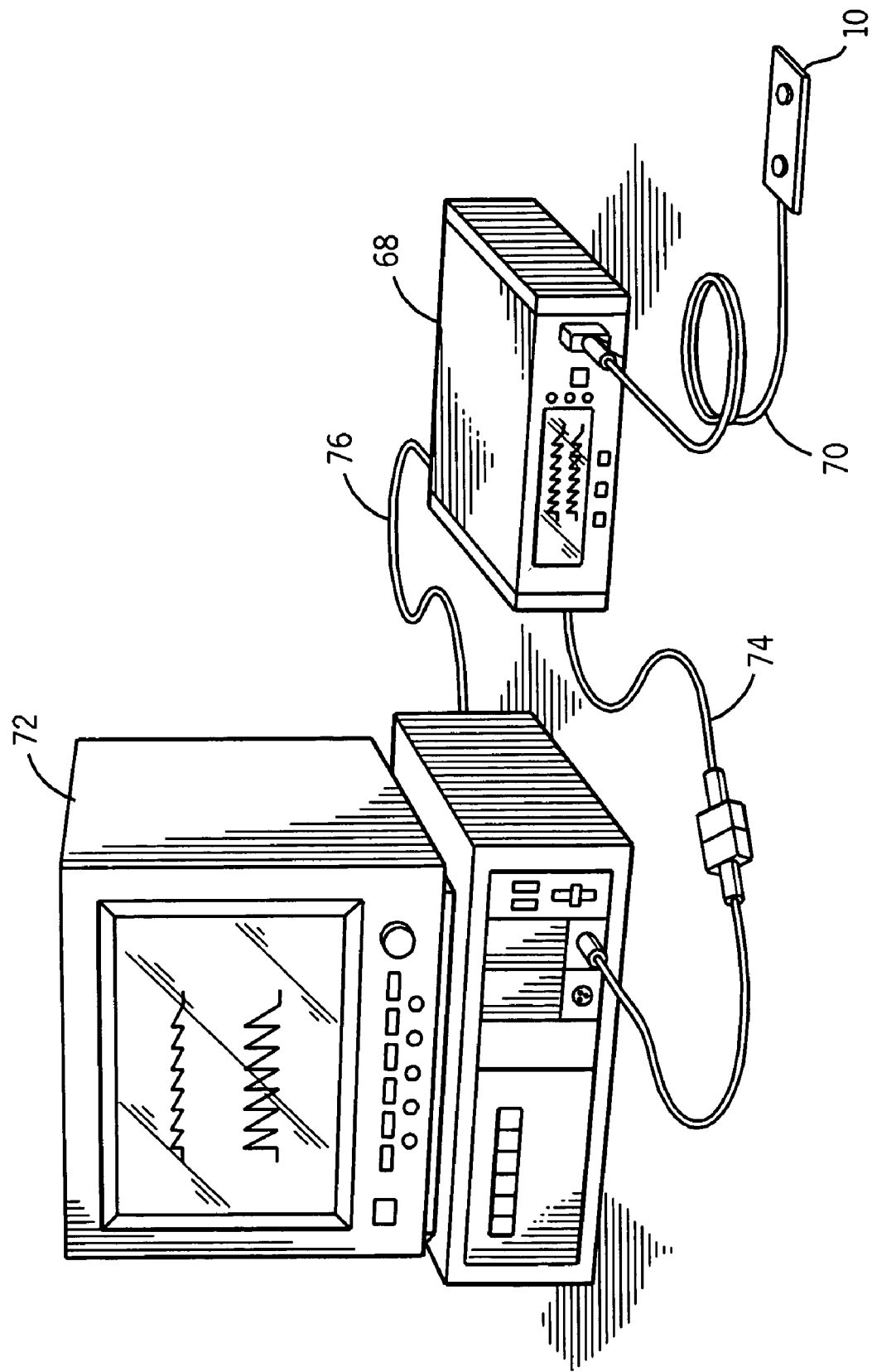
FIG. 7 illustrates a pulse oximetry system coupled to a multi-parameter patient monitor and a sensor according to embodiments of the present invention.

It should be understood that the sensors discussed above may be used in conjunction with a pulse oximetry monitor 68, as illustrated in FIG. 7. It should be appreciated that the cable 70 of the sensor 10 may be coupled to the monitor 68 or it may be coupled to a transmission device (not shown) to facilitate wireless transmission between the sensor 10 and the monitor 68. The monitor 68 may be any suitable pulse oximeter, such as those available from Nellcor Puritan Bennett Inc. Furthermore, to upgrade conventional pulse oximetry provided by the monitor 68 to provide additional functions, the monitor 68 may be coupled to a multi-parameter patient monitor 72 via a cable 74 connected to a sensor input port or via a cable 76 connected to a digital communication port.

It should also be understood that the sensors described herein include an emitter and a detector that may be of any suitable type. For example, the emitter may be one or more light emitting diodes adapted to transmit one or more wavelengths of light in the red to infrared range, and the detector may be a photodetector selected to receive light in the range or ranges emitted from the emitter. The emitter and the detector may be disposed on the sensor body, which may incorporate a shape memory material and that may be combined with any other suitable material, such as plastic, rubber, silicone, foam, woven material, or paper. Alternatively, the emitter and the detector may be remotely located and optically coupled to the sensor 10 using optical fibers. Although not shown in the embodiments discussed above, the sensors are typically coupled to a cable 70 that is responsible for transmitting electrical and/or optical signals to and from the emitter and detector of the sensor 10. The cable 70 may be permanently coupled to the sensor 10, or it may be removably coupled to the sensor 10—the latter alternative being more useful and cost efficient in situations where the sensor 10 is disposable.

The sensor 10 may be a "transmission type" sensor. Transmission type sensors include an emitter and detector that are typically placed on opposing sides of the sensor site. If the sensor site is a fingertip, for example, the sensor 10 is positioned over the patient's fingertip such that the emitter and detector lie on either side of the patient's nail bed. In other words, the sensor 10 is positioned so that the emitter is located on the patient's fingernail and the detector is located 180° opposite the emitter on the patient's finger pad. During operation, the emitter shines one or more wavelengths of light through the patient's fingertip and the light received by the detector is processed to determine various physiological characteristics of the patient. In each of the embodiments discussed herein, it should be understood that the locations of the emitter and the detector may be exchanged. For example, the detector may be located at the top of the finger and the emitter may be located underneath the finger. In either arrangement, the sensor 10 will perform in substantially the same manner.

Although the embodiments described herein generally referred to transmission type sensors, it should be understood that the sensor 10 may be a reflectance type sensor. Reflectance type sensors generally operate under the same general principles as transmittance type sensors. However, reflectance type sensors include an emitter and detector that are typically placed on the same side of the sensor site. For example, a reflectance type sensor may be placed on a patient's fingertip, nose bridge, or earlobe such that the emitter and detector lie side-by-side. Reflectance type sensors detect light photons that are scattered back to the detector.

For pulse oximetry applications using either transmission or reflectance type sensors, the oxygen saturation of the patient's arterial blood may be determined using two or more wavelengths of light, most commonly red and near infrared wavelengths. Similarly, in other applications a tissue water fraction (or other body fluid related metric) or a concentration of one or more biochemical components in an aqueous environment may be measured using two or more wavelengths of light, most commonly near infrared wavelengths between about 1,000 nm to about 2,500 nm. It should be understood that, as used herein, the term "light" may refer to one or more of infrared, visible, ultraviolet, or even X-ray electromagnetic radiation, and may also include any wavelength within the infrared, visible, ultraviolet, or X-ray spectra.

While the invention may be susceptible to various modifications and alternative forms, specific embodiments have been shown by way of example in the drawings and have been described in detail herein. However, it should be understood that the invention is not intended to be limited to the particular forms disclosed. Indeed, the present techniques may not only be applied to measurements of blood oxygen saturation, but these techniques may also be utilized for the measurement and/or analysis of other blood constituents using principles of pulse oximetry. Rather, the invention is to cover all modifications, equivalents, and alternatives falling within the spirit and scope of the invention as defined by the following appended claims.

What is claimed is:

1. A sensor adapted to be applied to a patient's tissue comprising:
   a sensor body comprising a material with shape memory, wherein the sensor body is adapted to assume a substantially curved configuration in the absence of a deforming force and wherein the sensor is adapted to apply a spring force to the patient's tissue adapted to overcome a blood pressure of about 10 mm Hg to about 80 mm Hg; and
   at least one sensing element disposed on the sensor body.

2. The sensor, as set forth in claim 1, wherein the sensor comprises at least one of a pulse oximetry sensor or a sensor for measuring a water fraction, or a combination thereof.

3. The sensor, as set forth in claim 1, wherein the at least one sensing element comprises an emitter and a detector.

4. The sensor, as set forth in claim 3, wherein the emitter comprises at least one light emitting diode and wherein the detector comprises at least one photodetector.

5. The sensor, as set forth in claim 1, wherein the material with shape memory is configured to form a flat spring.

6. The sensor, as set forth in claim 1, wherein the material with shape memory is configured to form a strap.

7. The sensor, as set forth in claim 1, comprising an adhesive material disposed on a tissue-contacting surface of the sensor.

8. The sensor, as set forth in claim 1, wherein the sensor is adapted to be used on a finger, toe, ear, or nose.

9. The sensor, as set forth in claim 1, wherein the material with shape memory comprises a shape memory metal.

10. A sensor adapted to be applied to a patient's tissue comprising:
    a sensor body comprising a material with shape memory, wherein the sensor body is adapted to assume a substantially curved configuration in the absence of a deforming force;
    at least one sensing element disposed on the sensor body; and
    a restraining element adapted to hold the sensor body in a substantially planar configuration.

11. The sensor, as set forth in claim 10, wherein the restraining element comprises a breakable component.

12. The sensor, as set forth in claim 10, wherein the restraining element comprises a peelable adhesive layer disposed on the sensor body.

13. The sensor, as set forth in claim 10, wherein the restraining element comprises a hollow sleeve adapted to slide over at least one end of the sensor.

14. A pulse oximetry system comprising:
    a pulse oximetry monitor; and
    a pulse oximetry sensor adapted to be operatively coupled to the monitor, the sensor comprising:
       a sensor body comprising a material with shape memory, wherein the sensor body is adapted to assume a substantially curved configuration in the absence of a deforming force and wherein the sensor is adapted to apply a spring force to the patient's tissue adapted to overcome a blood pressure of about 10 mm Hg to about 80 mm Hg; and
       at least one sensing element disposed on the sensor body.

15. The pulse oximetry system, as set forth in claim 14, wherein the sensor comprises a sensor for measuring a water fraction.

16. The pulse oximetry system, as set forth in claim 14, wherein the at least one sensing element comprises an emitter and a detector.

17. The pulse oximetry system, as set forth in claim 16, wherein the emitter comprises at lest one light emitting diode and wherein the detector comprises at least one photodetector.

18. The pulse oximetry system, as set forth in claim 14, wherein the material with shape memory is configured to form a flat spring.

19. The pulse oximetry system, as set forth in claim 14, wherein the material with shape memory is configured to form a strap.

20. The pulse oximetry system, as set forth in claim 14, comprising an adhesive material disposed on a tissue-contacting surface of the sensor.

21. The pulse oximetry system, as set forth in claim 14, wherein the sensor is adapted to be used on a finger, toe, ear, or nose.

22. The pulse oximetry system, as set forth in claim 14, wherein the material with shape memory comprises a shape memory metal.

23. A pulse oximetry system comprising:
    a pulse oximetry monitor; and
    a pulse oximetry sensor adapted to be operatively coupled to the monitor, the sensor comprising:
       a sensor body comprising a material with shape memory, wherein the sensor body is adapted to assume a substantially curved configuration in the absence of a deforming force:
    at least one sensing element disposed on the sensor body; and
    a restraining element adapted to hold the sensor body in a substantially planar configuration.

24. The pulse oximetry system, as set forth in claim 23, wherein the restraining element comprises a breakable component.

25. The pulse oximetry system, as set forth in claim 23, wherein the restraining element comprises a peelable adhesive layer disposed on the sensor body.

26. The pulse oximetry system, as set forth in claim 23, wherein the restraining element comprises a hollow sleeve adapted to slide over at least one end of the sensor.

27. A sensor packaging system comprising:
a protective package having an interior to hold at least one sensor in a substantially planar position in the interior of the protective package; and at least one sensor, the sensor comprising:
at least one sensing element; and
a material having shape memory, wherein the sensor is adapted to be curved in the absence of a deforming force, and wherein the sensor is restrained in a substantially planar position.

28. The packaging system, as set forth in claim 27, wherein the sensor comprises at least one of a pulse oximetry sensor or a sensor for measuring a water fraction.

29. The packaging system, as set forth in claim 27, wherein the sensing element comprises an emitter and a detector.

30. The packaging system, as set forth in claim 29, wherein the emitter comprises a light-emitting diode and the detector comprises at least one photodetector.

31. The packaging system, as set forth in claim 27, wherein the sensor is restrained with a breakable component disposed on the sensor body.

32. The packaging system, as set forth in claim 27, wherein the sensor is restrained with a peelable adhesive layer disposed on the sensor body.

33. The packaging system, as set forth in claim 27, wherein the sensor is restrained with a hollow sleeve adapted to slide over at least one end of the sensor.

34. The packaging system, as set forth in claim 27, wherein the sensor is restrained by a restraining element disposed on the protective package.

35. The packaging system, as set forth in claim 27, wherein the material with shape memory is configured to form a flat spring.

36. The packaging system, as set forth in claim 27, wherein the material with shape memory is configured to form a strap.

37. The packaging system, as set forth in claim 27, wherein the sensor comprises an adhesive material disposed on a tissue-contacting surface of the sensor.

38. A method for packaging a sensor comprising:
providing a substantially curved sensor body comprising a material with shape memory;
deforming the sensor body into a substantially flat position;
restraining the sensor body in the substantially flat position; and
packaging the sensor in a packaging container.

39. The method, as set forth in claim 38, wherein restraining the sensor comprises using a restraining element disposed on the sensor body.

40. The method, as set forth in claim 39, wherein the restraining element comprises a peelable adhesive layer, a hollow sleeve, or a breakable component.

41. The method, as set forth in claim 38, wherein restraining the sensor comprises using a restraining element disposed on the packaging container.

42. The method, as set forth in claim 38, wherein the sensor comprises an adhesive material disposed on a tissue-contacting surface of the sensor.

43. A method of manufacturing a sensor, comprising:
providing a sensor body comprising a material with shape memory, wherein the sensor body is adapted to assume a substantially curved configuration in the absence of a deforming force and wherein the sensor body is adapted to apply a spring force to the patient's tissue to overcome a blood pressure of about 10 mm Hg to about 80 mm Hg; and
providing at least one sensing element disposed on the sensor body.

44. The method, as set forth in claim 43, wherein the material with shape memory is configured to form a flat spring.

45. The method, as set forth in claim 43, wherein the material with shape memory is configured to form a strap.

46. The method, as set forth in claim 43, wherein the sensing element comprises an emitter and a detector.

47. The method, as set forth in claim 43, comprising:
providing an adhesive material disposed on a tissue-contacting surface of sensor body.

48. A method of manufacturing a sensor, comprising:
providing a sensor body comprising a material with shape memory, wherein the sensor body is adapted to assume a substantially curved configuration in the absence of a deforming force;
providing at least one sensing element disposed on the sensor body; and
providing a restraining element adapted to hold the sensor body in a substantially planar configuration.

49. The method, as set forth in claim 48, wherein the restraining element comprises a breakable component disposed on the sensor body.

50. The method, as set forth in claim 48, wherein the restraining element comprises a peelable adhesive layer disposed on the sensor body.

51. The method, as set forth in claim 48, wherein the restraining element comprises a hollow sleeve adapted to slide over at least one end of the sensor.

* * * * *